United States Patent
Okada et al.

(10) Patent No.: US 11,317,897 B2
(45) Date of Patent: May 3, 2022

(54) ULTRASONIC ENDOSCOPE AND METHOD FOR MANUFACTURING SAME

(71) Applicant: FUJIFILM Corporation, Tokyo (JP)

(72) Inventors: Satoru Okada, Ashigara-kami-gun (JP); Katsuya Yamamoto, Ashigara-kami-gun (JP); Yasuhiko Morimoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 470 days.

(21) Appl. No.: 16/235,439

(22) Filed: Dec. 28, 2018

(65) Prior Publication Data

US 2019/0133559 A1     May 9, 2019

Related U.S. Application Data

(63) Continuation of application No. PCT/JP2017/014989, filed on Apr. 12, 2017.

(30) Foreign Application Priority Data

Jun. 30, 2016 (JP) .............................. JP2016-130194

(51) Int. Cl.
*A61B 8/00*     (2006.01)
*A61B 8/12*     (2006.01)
(Continued)

(52) U.S. Cl.
CPC ............ *A61B 8/546* (2013.01); *A61B 1/0011* (2013.01); *A61B 1/00114* (2013.01);
(Continued)

(58) Field of Classification Search
CPC ..... A61B 8/546; A61B 8/4477; A61B 8/4483; A61B 8/4494; A61B 8/445; A61B 8/4488;
(Continued)

(56) References Cited

U.S. PATENT DOCUMENTS

| | | | | |
|---|---|---|---|---|
| 5,721,463 A | * | 2/1998 | Snyder | .................. A61B 8/546 |
| | | | | 310/327 |
| 2005/0165314 A1 | * | 7/2005 | Tanaka | .................... A61B 8/12 |
| | | | | 600/459 |

(Continued)

FOREIGN PATENT DOCUMENTS

| | | |
|---|---|---|
| CN | 1726872 A | 2/2006 |
| CN | 101396289 A | 4/2009 |

(Continued)

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2017/014989, dated Jan. 10, 2019, with English translation of the Written Opinion.

(Continued)

*Primary Examiner* — Sean D Mattson
(74) *Attorney, Agent, or Firm* — Birch, Stewart, Kolasch & Birch, LLP

(57) ABSTRACT

The invention has, at a distal end part thereof, an ultrasonic oscillator array in which a plurality of ultrasonic oscillators are arranged; a shielded cable including a plurality of signal lines, and a plurality of metallic shield members disposed outside the signal lines; a wiring part including a plurality of connecting parts that electrically connect the plurality of signal lines to the plurality of ultrasonic oscillators, respectively; a ground part that is electrically connected to the plurality of shield members and has heat conductivity; a sheet-like first heat-conduction member disposed on a side surface of the ultrasonic oscillator array; and a second heat-conduction member that thermally connects the first heat-conduction member to the ground part. Accordingly, an ultrasonic endoscope capable of improving diagnostic accu- (Continued)

racy in ultrasonic diagnosis, and a method for manufacturing the ultrasonic endoscope are provided.

20 Claims, 15 Drawing Sheets

(51) Int. Cl.
| | |
|---|---|
| A61B 1/00 | (2006.01) |
| A61B 1/12 | (2006.01) |
| B06B 1/06 | (2006.01) |
| H01L 41/04 | (2006.01) |
| H01L 41/047 | (2006.01) |
| H01L 41/29 | (2013.01) |
| H01R 9/05 | (2006.01) |
| H01R 4/02 | (2006.01) |

(52) U.S. Cl.
CPC .............. *A61B 1/128* (2013.01); *A61B 8/12* (2013.01); *A61B 8/445* (2013.01); *A61B 8/4477* (2013.01); *A61B 8/4483* (2013.01); *A61B 8/4488* (2013.01); *A61B 8/4494* (2013.01); *B06B 1/0622* (2013.01); *H01L 41/04* (2013.01); *H01L 41/0475* (2013.01); *H01L 41/29* (2013.01); *H01R 9/0512* (2013.01); *B06B 2201/76* (2013.01); *H01R 4/023* (2013.01)

(58) Field of Classification Search
CPC ..... A61B 8/12; A61B 1/0011; A61B 1/00114; A61B 1/128; B06B 1/0622; B06B 2201/76; H01L 41/04; H01L 41/0475; H01L 41/29; H01R 9/0512; H01R 4/023
See application file for complete search history.

(56) References Cited

U.S. PATENT DOCUMENTS

| | | | |
|---|---|---|---|
| 2006/0025691 | A1 | 2/2006 | Tanaka et al. |
| 2009/0062656 | A1 | 3/2009 | Hyuga |
| 2009/0088646 | A1 | 4/2009 | Nagano et al. |
| 2009/0088647 | A1* | 4/2009 | Nagano ................. A61B 8/12 600/463 |
| 2009/0234233 | A1* | 9/2009 | Nagano ................. A61B 8/12 600/462 |
| 2010/0179430 | A1 | 7/2010 | Sano et al. |
| 2014/0046190 | A1* | 2/2014 | Ogawa ............... A61B 8/4444 600/462 |
| 2015/0289852 | A1 | 10/2015 | Cho et al. |
| 2015/0340129 | A1 | 11/2015 | Huang et al. |
| 2015/0359420 | A1* | 12/2015 | Hatase ............... A61B 1/0011 600/110 |
| 2016/0278737 | A1* | 9/2016 | Fujimura ........... A61B 8/4483 |
| 2017/0172402 | A1* | 6/2017 | Wakabayashi ........ A61B 1/018 |

FOREIGN PATENT DOCUMENTS

| | | |
|---|---|---|
| CN | 101444430 A | 6/2009 |
| CN | 101636112 A | 1/2010 |
| CN | 103648404 A | 3/2014 |
| CN | 104780855 A | 7/2015 |
| CN | 105097121 A | 11/2015 |
| EP | 0782125 A2 | 7/1997 |
| JP | 2009-60501 A | 3/2009 |
| JP | 5329065 B2 | 10/2013 |
| JP | 2014-57136 A | 3/2014 |

OTHER PUBLICATIONS

International Search Report (form PCT/ISA/210) for International Application No. PCT/JP2017/014989 dated Jul. 4, 2017, with English Translation.
Chinese Office Action and Search Report for corresponding Chinese Application No. 201780039789.3, dated Jan. 6, 2021, with English translation of the Office Action.
Extended European Search Report for European Application No. 17819600.2, dated Jul. 22, 2019.
European Office Action, dated May 19, 2020, for corresponding European Application No. 17819600.2.
Chinese Office Action and Search Report for Chinese Application No. 201780039789.3, dated Aug. 4, 2021, with English translation of the Office Action.

* cited by examiner

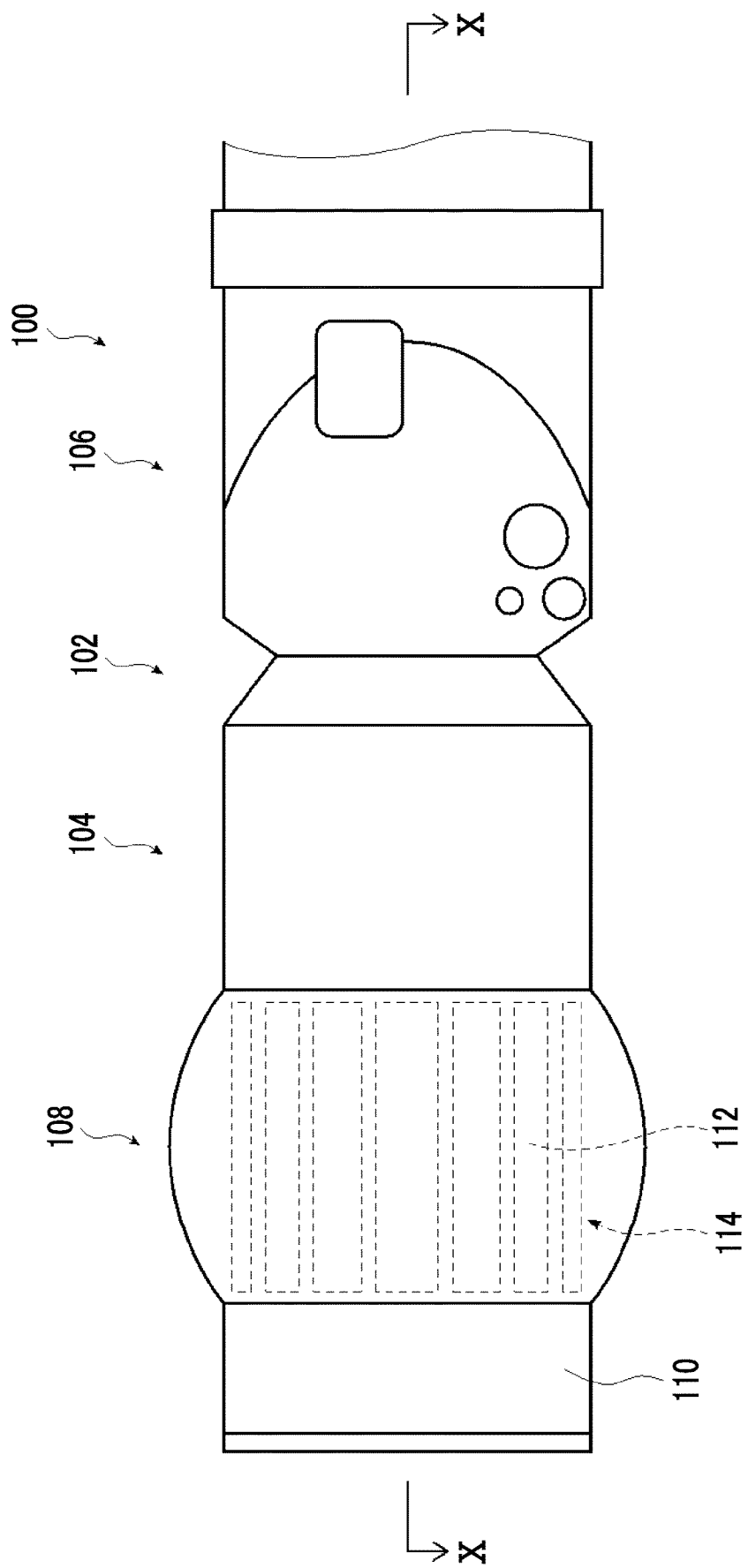

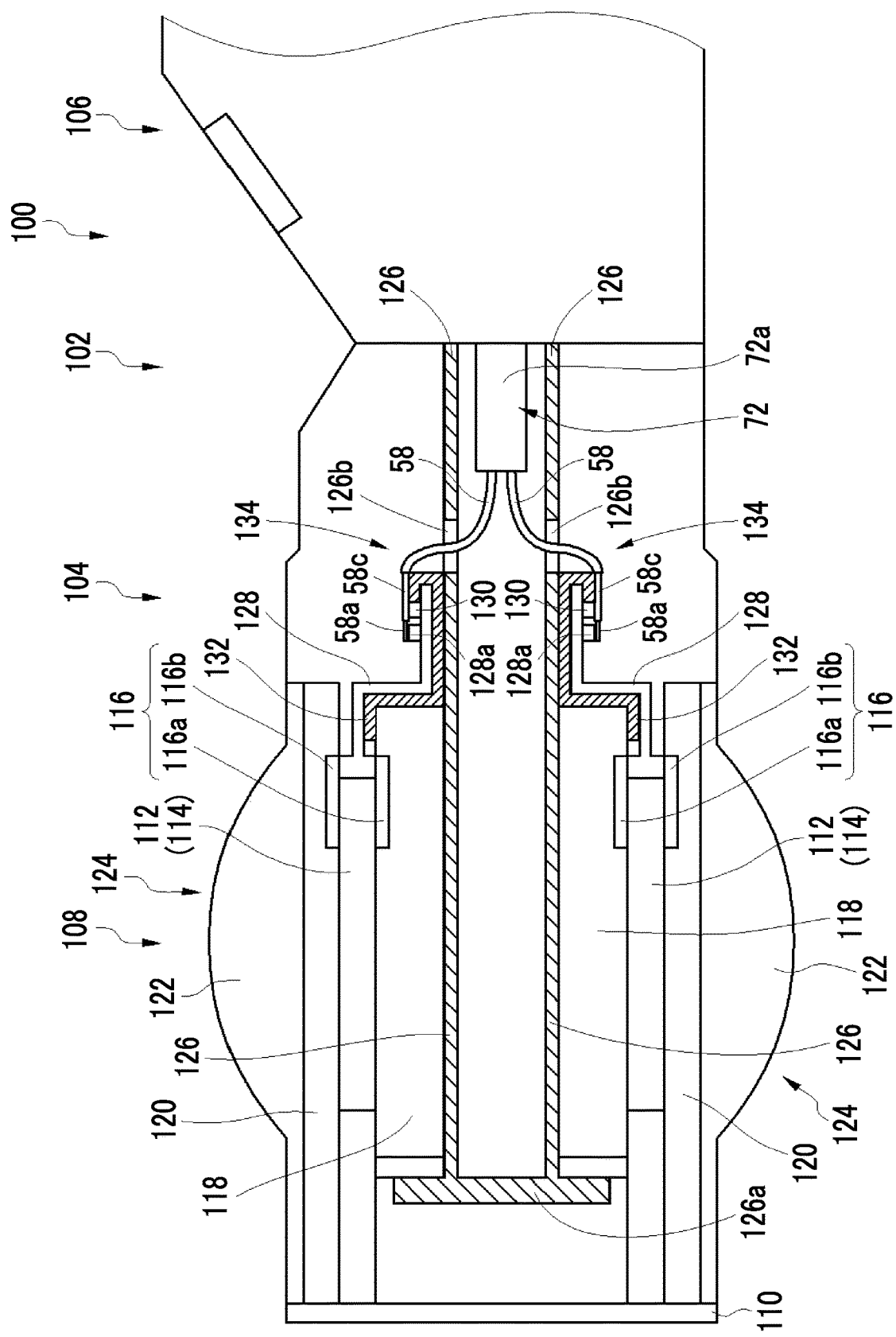

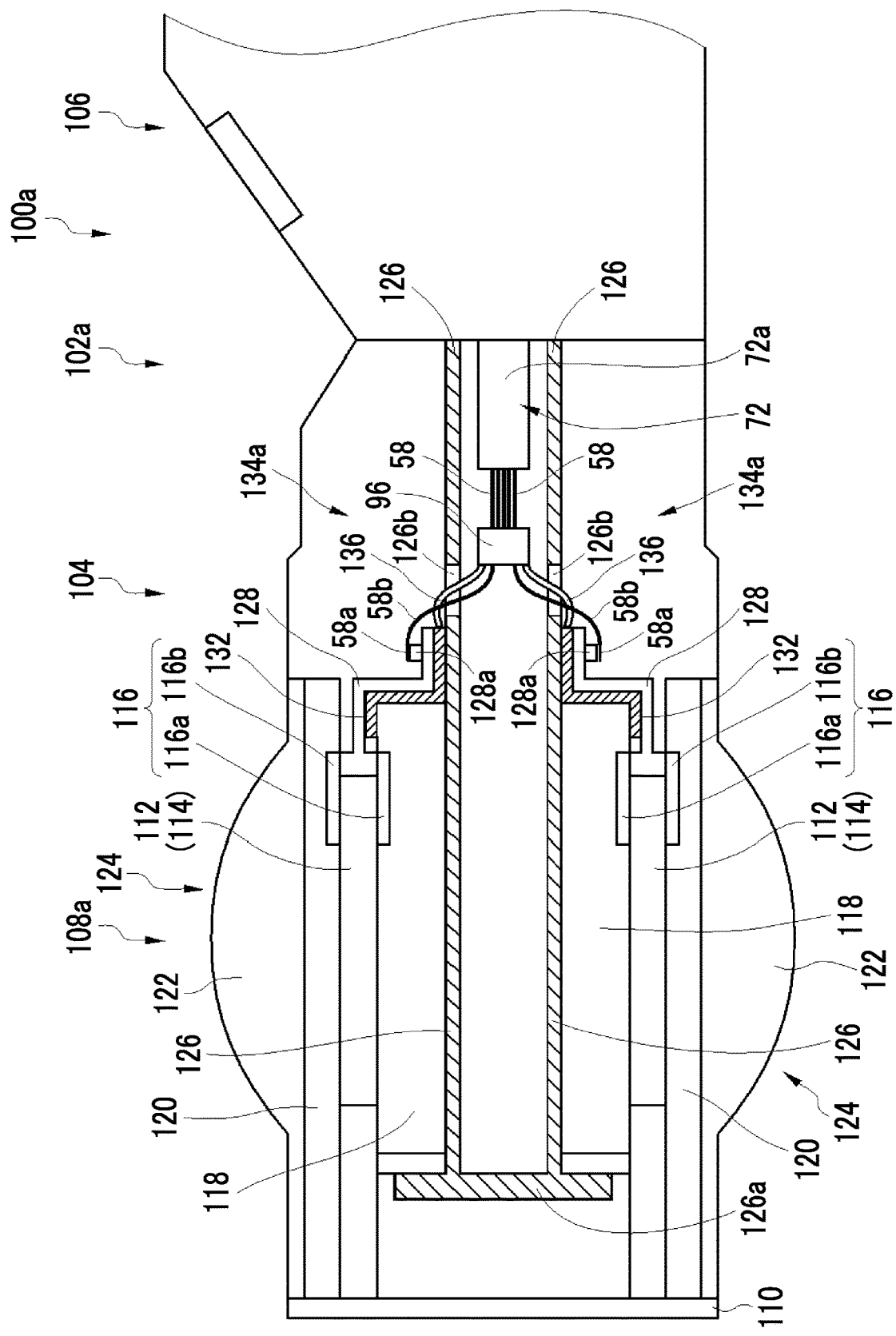

ULTRASONIC ENDOSCOPE AND METHOD FOR MANUFACTURING SAME

CROSS-REFERENCE TO RELATED APPLICATIONS

This application is a Continuation of PCT International Application No. PCT/JP2017/014989 filed on Apr. 12, 2017, which claims priority under 35 U.S.C. § 119(a) to Japanese Patent Application No. 2016-130194 filed on Jun. 30, 2016. The above application is hereby expressly incorporated by reference, in its entirety, into the present application.

BACKGROUND OF THE INVENTION

1. Field of the Invention

The invention relates to an ultrasonic endoscope and a method for manufacturing the same, and particularly, to an ultrasonic endoscope having a heat dissipation structure for radiating heat generated in micro ultrasonic oscillators used for the ultrasonic endoscope to be inserted into a body cavity, at a distal end part thereof, and a method of manufacturing the ultrasonic endoscope.

2. Description of the Related Art

Ultrasound diagnostic apparatuses using ultrasonic imaging generally include a body surface ultrasound probe that is used in contact with a subject or a body cavity ultrasound probe used while being inserted into a body cavity of the subject. Moreover, ultrasonic endoscopes in which an endoscope for optically observing the inside of the subject, and the body cavity ultrasound probe are combined together have recently been used. In a case where the ultrasound probe is used to transmit an ultrasonic beam toward the subject, such as a human body, and receive ultrasound echoes generated in the subject are received, ultrasound image information is acquired.

On the basis of this ultrasound image information, an ultrasound image of objects (for example, internal organs, diseased tissue, and the like) that are present within the subject is displayed on a display unit of an ultrasonic endoscope device body connected to an ultrasonic endoscope.

Generally, a plurality of ultrasonic oscillators (piezoelectric oscillators) in which electrodes are formed on both surfaces of a material (piezoelectric body) that exhibits develops the piezoelectric effect are used as an ultrasonic transducer (ultrasonic oscillator array) that transmits and receives ultrasonic waves.

In a case where a voltage is applied to the electrodes of the ultrasonic oscillators, the piezoelectric body expands and contracts due to the piezoelectric effect, and ultrasonic waves are generated. The ultrasonic beam transmitted in a desired direction can be formed by arranging the plurality of ultrasonic oscillators in one dimension or two dimensions to form the ultrasonic oscillator array and sequentially the plurality of driving the ultrasonic oscillators.

Additionally, the ultrasonic oscillators receive the propagating ultrasonic waves, thereby expanding and contracting to create electrical signals. The electrical signals are used as detection signals of the ultrasonic waves.

The ultrasonic endoscopes including such a plurality of ultrasonic oscillators are ones in which an ultrasonic observation part is provided at a distal end part of an endoscope with observation of the gallbladder or the pancreas by an alimentary canal as a main purpose. An optical sensor, illumination means, an air supply port, a water supply port, and a suction port in addition to the ultrasonic observation part are provided at the distal end part of the ultrasonic endoscope, similarly to ordinary endoscopes that are not provided with the ultrasonic observation part. In this way, in the ultrasonic endoscopes inserted into within the body cavity of the subject, particularly, into an upper gastrointestinal tract, a bronchus, or the like, in order to alleviate a physical burden on the subject, it is required to reduce the diameter of the insertion part of the ultrasonic endoscope and reduce the size of the distal end part, particularly, the ultrasonic observation part.

Additionally, in the distal end part of the ultrasonic endoscope, there are heat generation factors, such as the ultrasonic oscillators and a light source of the endoscope. However, since the insertion part, particularly, the distal end part of the ultrasonic endoscope directly comes into contact with the inside of the living body, such as a human body, it is required that the surface temperature of the insertion part should be equal to or lower than a predetermined temperature for safety reasons of preventing a low-temperature burn.

Thus, ultrasonic endoscopes having means for lowering the surface temperature of the distal end part while keeping size of the distal end part small are required. In recent years, various proposals for cooling a distal end part of an ultrasonic endoscope that is a heat generation source have been considered (refer to JP5329065B).

JP5329065B discloses an ultrasonic endoscope including an insertion part having a bending part. The insertion part has a backing material having a front surface on which a plurality of ultrasonic transducers are disposed, a sheathing member that houses the plurality of ultrasonic transducers at a distal end of the insertion part, and a heat-conduction member that is disposed within the sheathing member and is contact with a back surface of the backing material and an inner surface of the sheathing member. According to this configuration, the heat generated in the ultrasonic transducers and transferred to the backing material, and the heat generated in the backing material by ultrasonic waves being received by the ultrasonic transducers are transferred to the heat-conduction member via the backing material, and is further transferred to the sheathing member via the heat-conduction member, and is dissipated from the sheathing member to the outside of the ultrasonic endoscope. Therefore, in JP5329065B, heat dissipation from an ultrasonic transducer part to the outside is promoted.

SUMMARY OF THE INVENTION

Meanwhile, in the ultrasonic endoscope disclosed in JP5329065B, only a heat dissipation path along which the heat generated in the ultrasonic oscillators and the backing material layer is dissipated to the sheathing member via the heat-conduction member is taken into consideration. Therefore, there is a problem that a further improvement in the heat dissipation effect cannot be expected. Moreover, in the technique disclosed in JP5329065B, heat does not stay in the ultrasonic oscillators and the backing material layer, and is dissipated to the sheathing member. Therefore, the heat is dissipated to the inside of the body cavity near the distal end part of the ultrasonic endoscope. Here, since the heat is diffused from a sheathing member, a temperature rise is suppressed to some extent. However, there are problems that the heat may raise the temperature of the sheathing member of the distal end part of the ultrasonic endoscope and the temperature around the distal end part.

Nowadays, in the ultrasonic endoscopes, in order to improve diagnostic accuracy, receiving sensitivity is enhanced by laminating the ultrasonic transducers (oscillators) to increase the transmission output of the ultrasonic waves or increasing the number of ultrasonic oscillators.

As a result, there are possibilities the amount of heat dissipated from the ultrasonic oscillator may increase large, and the temperature of the insertion part that is contact with the inner wall of the body cavity, particularly, the distal end part where the ultrasonic oscillators are disposed may rise due to heat generation of the ultrasonic oscillators.

Moreover, in the ultrasonic endoscopes, in order to improve the quality or the like of an obtained ultrasound image to improve the diagnostic accuracy, increasing a driving voltage for driving the ultrasonic oscillator in addition to than enhancing the receiving sensitivity is also considered. However, there is a concern that a further temperature rise may be caused due to the heat generation of the ultrasonic oscillators (ultrasonic transducers) resulting from increasing the driving voltage.

In this way, in a case where the number of ultrasonic oscillators is increased, the driving voltage of the ultrasonic oscillators is raised, or the transmission output of the ultrasonic waves is increased in order to improve the diagnostic accuracy by improve the quality or the like of the ultrasound image, the technique disclosed in JP5329065B has a problem in that the temperature around the distal end part of the ultrasonic endoscope that directly comes into contact with the inside of the living body, such as a human body, the sheathing member, and the like may be raised to an allowable temperature or higher.

Therefore, it is necessary to suppress heat generation or a temperature rise while keeping the diameter of the insertion part and the size of the distal end part small. Particularly, how to dissipate the generated heat of the oscillators there has been an important issue.

An object of the invention is to solve the above related-art problems and to provide an ultrasonic endoscope that has a heat dissipation structure capable of efficiently radiating heat in the heat generated in ultrasonic oscillators while keeping the diameter of an insertion part and the size of a distal end part small, and that consequently, can improve diagnostic accuracy in ultrasonic diagnosis.

Additionally, another object of the invention is to provide a method of manufacturing an ultrasonic endoscope that can reliably and stably manufacture such an ultrasonic endoscope without damaging signal lines or the like connected to constituent members, for example, ultra-compact ultrasonic oscillators and without causing an increase in cost, in addition to above object.

In order to achieve the above object, an ultrasonic endoscope of a first aspect of the invention comprises, at a distal end part thereof, an ultrasonic oscillator array in which a plurality of ultrasonic oscillators are arranged; a shielded cable including a plurality of signal lines, and a plurality of metallic shield members disposed outside the signal lines; a wiring part including a plurality of connecting parts that electrically connect the plurality of signal lines to the plurality of ultrasonic oscillators, respectively; a ground part that is electrically connected to the plurality of shield members and has heat conductivity; a sheet-like first heat-conduction member disposed on a side surface of the ultrasonic oscillator array; and a second heat-conduction member that thermally connects the first heat-conduction member to the ground part.

Here, it is preferable that the shielded cable is at least one of a plurality of coaxial cables each including a signal line at a center side thereof and a shield member on an outer peripheral side of the signal line, or a non-coaxial cable in which the plurality of signal lines and a plurality of drain lines as the plurality of shield members are disposed in a mixed manner, or the plurality of signal lines are disposed on a center side of the cable, and a plurality of conducting wires are disposed as the plurality of shield members around the plurality of signal lines.

Additionally, it is preferable that the ultrasonic endoscope further comprises a backing material layer that is laminated on a back surface side of the ultrasonic oscillator array and supports the plurality of ultrasonic oscillators, the first heat-conduction member is disposed on a side surface of a laminated body including the ultrasonic oscillator array and the backing material layer, and extends to a lower side of the backing material layer that is a side opposite to the ultrasonic oscillator array side, the second heat-conduction member is integrated with the first heat-conduction member in advance at a lower end part of the first heat-conduction member that is the side opposite to the ultrasonic oscillator array side, the plurality of shield members constitute the ground part, and are respectively connected to the second heat-conduction member integrated with the first heat-conduction member, respectively, and the first heat-conduction member integrated with the second heat-conduction member is pasted on the plurality of ultrasonic oscillators.

Additionally, it is preferable that the first heat-conduction member is connected to the second heat-conduction member such that a lower end part of the first heat-conduction member on the side opposite to the ultrasonic oscillator array is directed to an upper side that is the ultrasonic oscillator array side, and an upper end part side of the first heat-conduction member is folded toward the side surface of the laminated body, and is pasted on the plurality of ultrasonic oscillators.

Additionally, it is preferable that the second heat-conduction member is a ground bar.

Additionally, it is preferable that the first heat-conduction member and the second heat-conduction member are conductive members, the plurality of connecting parts of the wiring part electrically connect the plurality of signal lines to the plurality of ultrasonic oscillators, respectively, using first solder, the plurality of shield members are connected to the second heat-conduction member using the first solder, respectively, and the first heat-conduction member is connected to the second heat-conduction member, using at least one of second solder having a lower melting point than the first solder, silver paste, or a conductive adhesive.

Additionally, it is preferable that the second heat-conduction member is a wired board including a ground bar, and the first heat-conduction member is electrically connected to the ground bar.

Additionally, it is preferable that the ground part is a common collective ground connected to the plurality of shield members, and the second heat-conduction member thermally connects the collective ground and the first heat-conduction member to each other.

Additionally, it is preferable that the second heat-conduction member is a cable thicker than the signal lines or a deformable metal-braided net member.

Additionally, it is preferable that the second heat-conduction member is an insulating heat-conduction member.

Additionally, it is preferable that the first heat-conduction member is metallic foil having electrical conductivity and heat conductivity.

Additionally, it is preferable that the metallic foil is copper foil, aluminum foil, or gold foil.

Additionally, in order to achieve the above other object, a method of manufacturing an ultrasonic endoscope of a second aspect of the invention comprises, when manufacturing the above ultrasonic endoscope of the above aspect, integrating the first heat-conduction member and the second heat-conduction member in advance at a lower end part of the first heat-conduction member that is the side opposite to the ultrasonic oscillator array side; connecting the plurality of shield members of the shielded cable to the second heat-conduction member integrated with the first heat-conduction member in advance, respectively; then, connecting the plurality of signal lines of the shielded cable, including the plurality of shield members connected to the second heat-conduction member integrated with the first heat-conduction member in advance, to the plurality of connecting parts of the wiring part, respectively, using solder, and electrically connecting the plurality of signal lines to the plurality of ultrasonic oscillators; and pasting the first heat-conduction member integrated with the second heat-conduction member to the plurality of ultrasonic oscillators, and disposing the first heat-conduction member on a side surface of a laminated body including the ultrasonic oscillator array and a backing material layer that is laminated on the back surface side of the ultrasonic oscillator array and supports the plurality of ultrasonic oscillators.

Here, it is preferable that in the step of connecting the plurality of shield members to the second heat-conduction member, respectively, the second heat-conduction member is the ultrasonic oscillator array side, the first heat-conduction member integrated with the second heat-conduction member is the side opposite to the ultrasonic oscillator array side, and the plurality of shield members are connected to the second heat-conduction member, respectively, and in the step of disposing the first heat-conduction member on the side surface of the laminated body, the first heat-conduction member is pasted on the plurality of ultrasonic oscillators and is disposed on the side surface of the laminated body in a state where the first heat-conduction member is folded, and a side of first heat-conduction member opposite to a side thereof to which the second heat-conduction member is connected is the ultrasonic oscillator array side.

Additionally, it is preferable that the second heat-conduction member is a ground bar, and in the step of integrating the first heat-conduction member and the second heat-conduction member with each other in advance, the ground bar and the first heat-conduction member are electrically connected to each other by integrating a wired board including the ground bar, and the first heat-conduction member with each other in advance.

Additionally, in order to achieve the above other object, a method of manufacturing an ultrasonic endoscope of a third aspect of the invention comprises, when manufacturing the ultrasonic endoscope of the above first aspect, pasting the first heat-conduction member to the plurality of ultrasonic oscillators, and disposing the first heat-conduction member on a side surface of a laminated body including the ultrasonic oscillator array and a backing material layer that is laminated on the back surface side of the ultrasonic oscillator array and supports the plurality of ultrasonic oscillators; connecting the plurality of shield members of the shielded cable to the second heat-conduction member, using solder, respectively; connecting the plurality of signal lines of the shielded cable to the plurality of connecting parts of the wiring part, respectively, using the solder, and electrically connecting the plurality of signal lines to the plurality of ultrasonic oscillators; and connecting the first heat-conduction member to the second heat-conduction member, using at least one of solder having a lower melting point than the solder, silver paste, or a conductive adhesive.

According to the invention, it is possible to provide the ultrasonic endoscope that has a heat dissipation structure capable of efficiently radiating heat in the heat generated in the ultrasonic oscillators while keeping the diameter of the insertion part and the size of the distal end part small, and that consequently, can improve diagnostic accuracy in ultrasonic diagnosis.

Namely, according to the invention, for example, by pasting the first heat-conduction member, such as the copper foil, on the plurality of ultrasonic oscillators, and connecting the first heat-conduction member to the ground part, such as the ground bar or the collective ground, via the second heat-conduction member, the heat generated in the plurality of ultrasonic oscillators and transferred to the first heat-conduction member can be efficiently escaped to the plurality of coaxial cables connected to the ground part, via the ground part, and can be efficiently dissipated to the outside of a subject. In addition, in the invention, the expression "connecting the first heat-conduction member to the ground part via the second heat-conduction member" is directly connecting the first heat-conduction member to the ground bar in a case where the ground bar serves as both the ground part and the second heat-conduction member, and connecting the first heat-conduction member to the collective ground via the second heat-conduction member in a case where the collective ground is the ground part.

Additionally, according to the invention, it is possible to reliably and stably manufacture such an ultrasonic endoscope without damaging the signal lines or the like connected to constituent members, for example, ultra-compact ultrasonic oscillators and without causing an increase in cost.

BRIEF DESCRIPTION OF THE DRAWINGS

FIG. 21 is a partially enlarged plan view schematically illustrating a distal end part of an insertion part of an ultrasonic endoscope of a still further embodiment of the invention.

FIG. 22 is a view taken along line X-X illustrated in FIG. 21 and seen from an arrow direction and is a partially longitudinal cross-sectional view of the distal end part of the insertion part of the ultrasonic endoscope illustrated in FIG. 21.

FIG. 23 is a partially cross-sectional view schematically illustrating a distal end part of an insertion part of an ultrasonic endoscope of a still further embodiment of the invention.

DESCRIPTION OF THE PREFERRED EMBODIMENTS

An ultrasonic endoscope and a method for manufacturing the ultrasonic endoscope related to the invention will be described below in detail on the basis of preferred embodiments illustrated in the accompanying drawings.

First Embodiment

Figure 1:
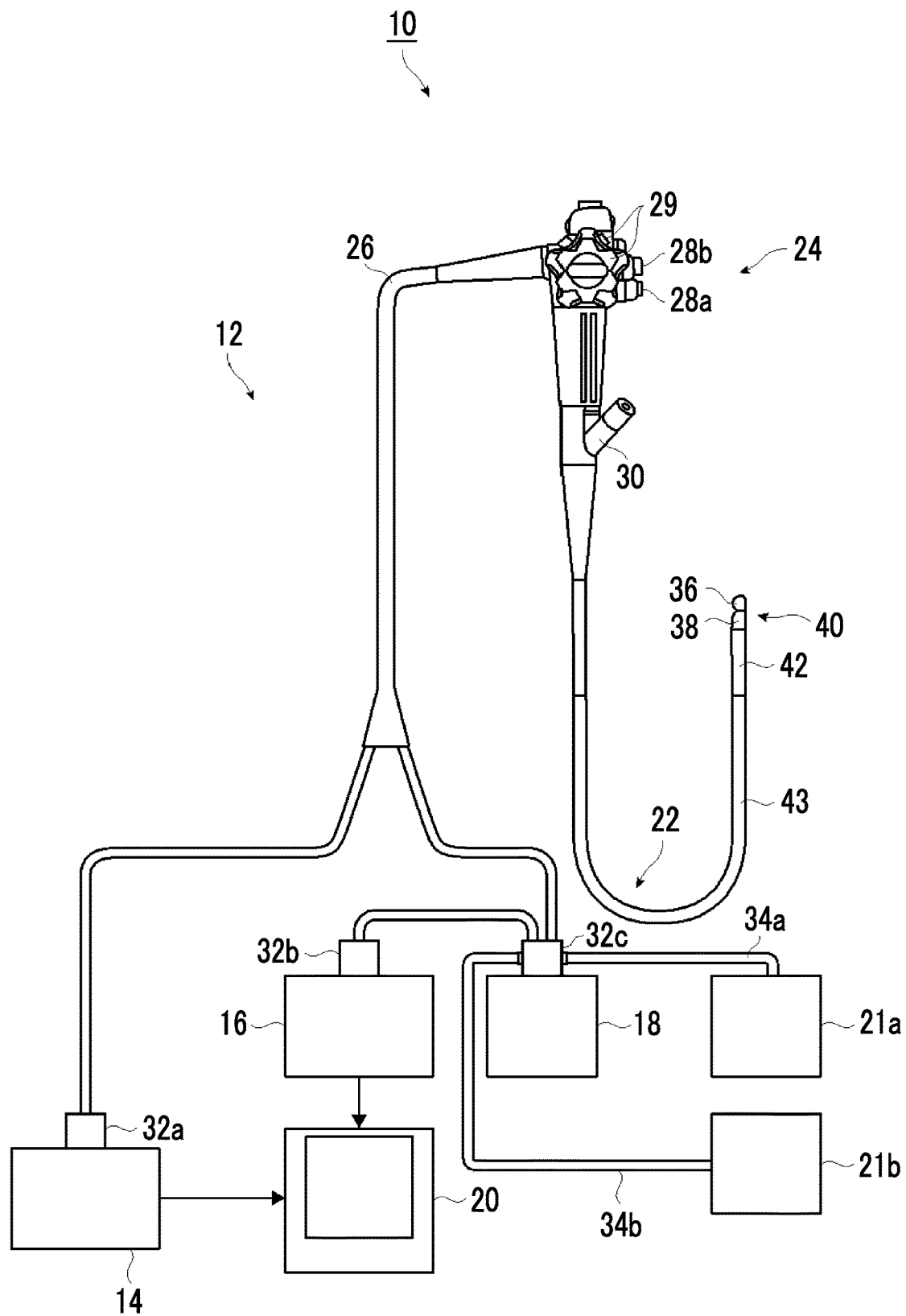
FIG. 1 is a schematic configuration view illustrating an example of the configuration of an ultrasonic inspection system using an ultrasonic endoscope of the invention.

FIG. 1 is a schematic configuration view illustrating an example of the configuration of an ultrasonic inspection system related to an ultrasonic endoscope according to a first embodiment of the invention.

An ultrasonic inspection system 10 illustrated in FIG. 1 allows observation of the gallbladder or the pancreas that is difficult in the ultrasonic inspection from the body surface of a subject, such as a patient, via alimentary canals, such as the esophagus, the stomach, the duodenum, the small intestine, and the large intestine that are body cavities of the subject, includes the ultrasonic oscillator unit of the invention, and acquires an ultrasound image of a region to be observed of the subject while inserting the ultrasonic endoscope of the invention having an ultrasonic observation part and an endoscope observation part into the body cavities of the subject to observe an endoscopic image of the subject. The ultrasonic observation part acquires an ultrasonic tomographic image (hereinafter referred to as the ultrasound image), and the endoscope observation part acquires an endoscopic optical image (hereinafter referred to as the endoscopic image).

As illustrated in FIG. 1, the ultrasonic inspection system 10 is configured to include an ultrasonic endoscope 12 of a first embodiment of the invention having a heat dissipation structure at a distal end part, an ultrasonic wave processor device 14 that creates the ultrasound image, an endoscope processor device 16 that creates the endoscopic image, a light source device 18 that supplies the illumination light for illuminating the inside of a body cavity to the ultrasonic endoscope 12, and a monitor 20 that displays the ultrasound image and/or the endoscopic image.

Additionally, the ultrasonic inspection system 10 further includes a water supply tank 21a that stores washing water or the like, and a suction pump 21b that suctions a suction object (including the supplied washing water) within the body cavity. In addition, although not illustrated, the ultrasonic inspection system 10 may further include a supply pump that supplies washing water within the water supply tank 21a or gas, such as external air, to a pipe line (not illustrated) within the ultrasonic endoscope 12.

First, the ultrasonic endoscope 12 of the invention has an ultrasonic observation part 36 including a heat dissipation structure (70: refer to FIGS. 3 to 5) serving as a feature of the invention, and an endoscope observation part 38, at a distal end part thereof, and images the inside of the body cavity of the subject to acquire the ultrasound image (echo signals) and the endoscopic image (image signals), respectively.

The ultrasonic endoscope 12 includes the ultrasonic observation part 36 and the endoscope observation part 38 at the distal end part thereof, and is constituted of an insertion part 22 inserted into the body cavity of the subject, an operating part 24 that is provided continuously with a proximal end part of the insertion part 22 to allow an operator, such as a doctor or an engineer to perform an operation, and a universal cord 26 has one end connected to the operating part 24.

An air/water supply button 28a that opens and closes an air/water supply pipe line (not illustrated) from the water supply tank 21a and a suction button 28b that open and close a suction pipe line (not illustrated) from the suction pump 21b are provided side by side at the operating part 24, and the operating part 24 is provided with a pair of angle knobs 29 and 29 and a treatment tool insertion port (a forceps port) 30.

Here, the water supply tank 21a is a tank for storing the washing water to be supplied to the air/water supply pipe line within the ultrasonic endoscope 12 for washing the endoscope observation part 38 and the like of the ultrasonic endoscope 12. In addition, the air/water supply button 28a is used to jet gas, such as air, and water, such as washing water, which has been supplied through the air/water supply pipe line from the water supply tank 21a, from the endoscope observation part 38 on a distal end side of the insertion part 22.

Additionally, the suction pump 21b suctions the suction pipe line (not illustrated) in order to suction the suction object within the body cavity (including the supplied washing water) from the distal end side of the ultrasonic endoscope 12. The suction button 28b is used to suction the suction object within the body cavity from the distal end side of the insertion part 22 with a suction force of the suction pump 21b.

Additionally, the treatment tool insertion port 30 is a port for allowing a treatment tool, such as forceps, a puncturing needle, or a high-frequency knife to be inserted therethrough.

The other end part of the universal cord 26 is provided with an ultrasonic wave connector 32a connected to the ultrasonic wave processor device 14, an endoscope connector 32b connected to the endoscope processor device 16, and a light source connector 32c connected to the light source device 18. The ultrasonic endoscope 12 is attachably and detachably connected to the ultrasonic wave processor device 14, the endoscope processor device 16, and the light source device 18 via the connectors 32a, 32b, and 32c, respectively. Additionally, an air/water supply tube 34a to which the water supply tank 21a is to be connected, a suction tube 34b to which the suction pump 21b is to be connected, and the like are connected to the light source connector 32c.

The insertion part 22 is constituted of the distal end part (distal end rigid part) 40 that is formed of a rigid member and has the ultrasonic observation part 36 and the endoscope observation part 38, a bending part 42 that is provided continuously with a proximal end side of the distal end part 40, is formed by coupling a plurality of bendable pieces to each other, and is bendable, and a flexible part 43 that couples a proximal end side of the bending part 42 and a distal end side of the operating part 24 to each other and is thin, elongated, and flexible, sequentially from the distal end side.

The bending part 42 is remotely bending-operated by rotationally moving the pair of angle knobs 29 and 29 provided at the operating part 24. Accordingly, the distal end part 40 can be directed to a desired direction.

Additionally, a balloon into which an ultrasonic transmission medium (for example, water, oil, or the like) for covering the ultrasonic observation part 36 is injected may be attachably and detachably mounted on the distal end part 40. Since ultrasonic waves and the echo signals are significantly damped in the air, the ultrasonic transmission medium is injected into the balloon to expand the balloon and is made to abut against the region to be observed. Accordingly, air can be eliminated from between an ultrasonic oscillator (ultrasonic transducer) array (50: refer to FIGS. 2 to 5) of the ultrasonic observation part 36 and the region to be observed, and the damping of the ultrasonic waves and the echo signals can be prevented.

In addition, the ultrasonic wave processor device 14 is a device for creating and supplying ultrasonic signals (data) for generating the ultrasonic waves in the ultrasonic oscillator array (50: refer to FIGS. 2 to 5) of the ultrasonic observation part 36 of the distal end part 40 of the insertion part 22 of the ultrasonic endoscope 12. Additionally, the ultrasonic wave processor device 14 is a device for receiving and acquiring the echo signals (data), which is reflected from the region to be observed to which the ultrasonic waves are radiated, with the ultrasonic oscillator array (50), and for creating the ultrasound image that is obtained by performed various kinds of signal (data) processing on the acquired echo signals and is displayed on the monitor 20.

The endoscope processor device 16 is a device for receiving and acquiring captured image signals (data) acquired from the region to be observed illuminated with the illumination light from the light source device 18 in the endoscope observation part 38 of the distal end part 40 of the insertion part 22 of the ultrasonic endoscope 12, and creating the endoscopic image that is obtained by performing various kinds of signal (data) processing and image processing on the acquired image signals and is displayed on the monitor 20.

In addition, the processor devices 14 and 16 may be constituted of processors, such as a personal computer (PC).

In order to image the region to be observed within the body cavity to acquire the image signals with the endoscope observation part 38 of the ultrasonic endoscope 12, the light source device 18 is a device for generating illumination light, such as white light consisting of three primary color lights, such as red light (R), green light (G), and blue light (B), or specific wavelength light to supply the illumination light to the ultrasonic endoscope 12 to propagate the illumination light with a light guide or the like within the ultrasonic endoscope 12 (not illustrated), and emitting the illumination light from the endoscope observation part 38 of the distal end part 40 of the insertion part 22 of the ultrasonic endoscope 12 for illuminating the region to be observed within the body cavity with the illumination light.

The monitor 20 receives respective video signals created by the ultrasonic wave processor device 14 and the endoscope processor device 16 to display the ultrasound image and the endoscopic image. As for the display of the ultrasound image and the endoscopic image, it is possible to appropriately display one of the images on the monitor 20 through switching and to simultaneously display both the images. In addition, a monitor for displaying the ultrasound image and a monitor for displaying the endoscopic image may be separately provided, or the ultrasound image and the endoscopic image may be displayed in any other forms.

Next, the configuration of the distal end part of the insertion part of the ultrasonic endoscope will be described in detail with reference to FIGS. 2 to 4.

Figure 2:
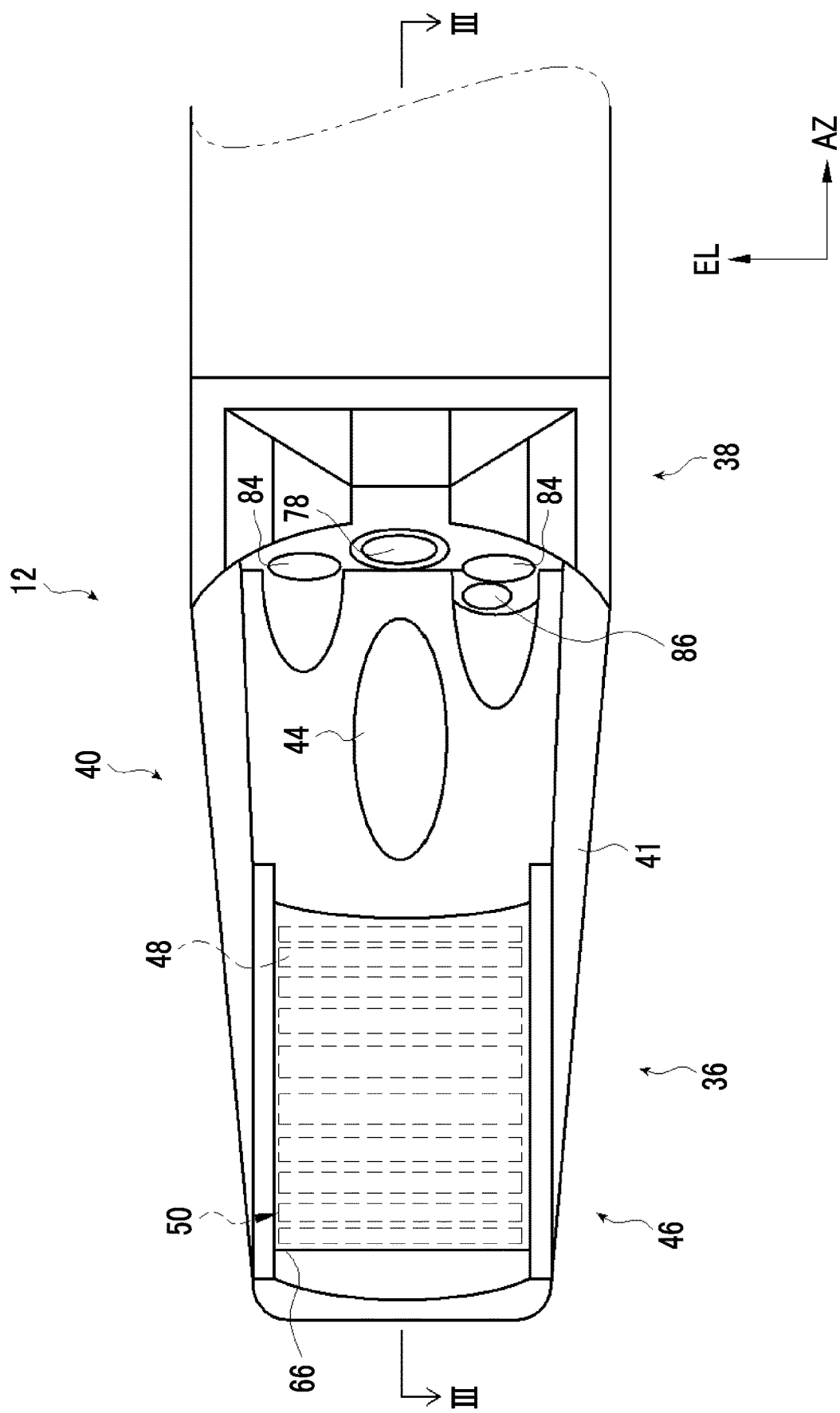
FIG. 2 is a partially enlarged plan view illustrating a distal end part of the ultrasonic endoscope illustrated in FIG. 1.

FIG. 2 is a partially enlarged plan view illustrating the distal end part of the ultrasonic endoscope illustrated in FIG. 1 and its vicinity. FIG. 3 is a view taken along line illustrated in FIG. 2 and seen from an arrow direction and is a schematic cross-sectional view of the distal end part of the ultrasonic endoscope illustrated in FIG. 2 cut by a centerline in a longitudinal direction thereof. FIG. 4 is a schematic partially-enlarged longitudinal cross-sectional view of the ultrasonic observation part of the distal end part of the ultrasonic endoscope illustrated in FIG. 3. FIG. 5 is a view taken along line V-V illustrated in FIG. 3 and seen from an arrow direction and is a schematic cross-sectional view cut by a centerline of a circular-arc structure of the ultrasonic oscillator array of the ultrasonic observation part of the distal end part of the ultrasonic endoscope illustrated in FIG. 2.

Figure 3:
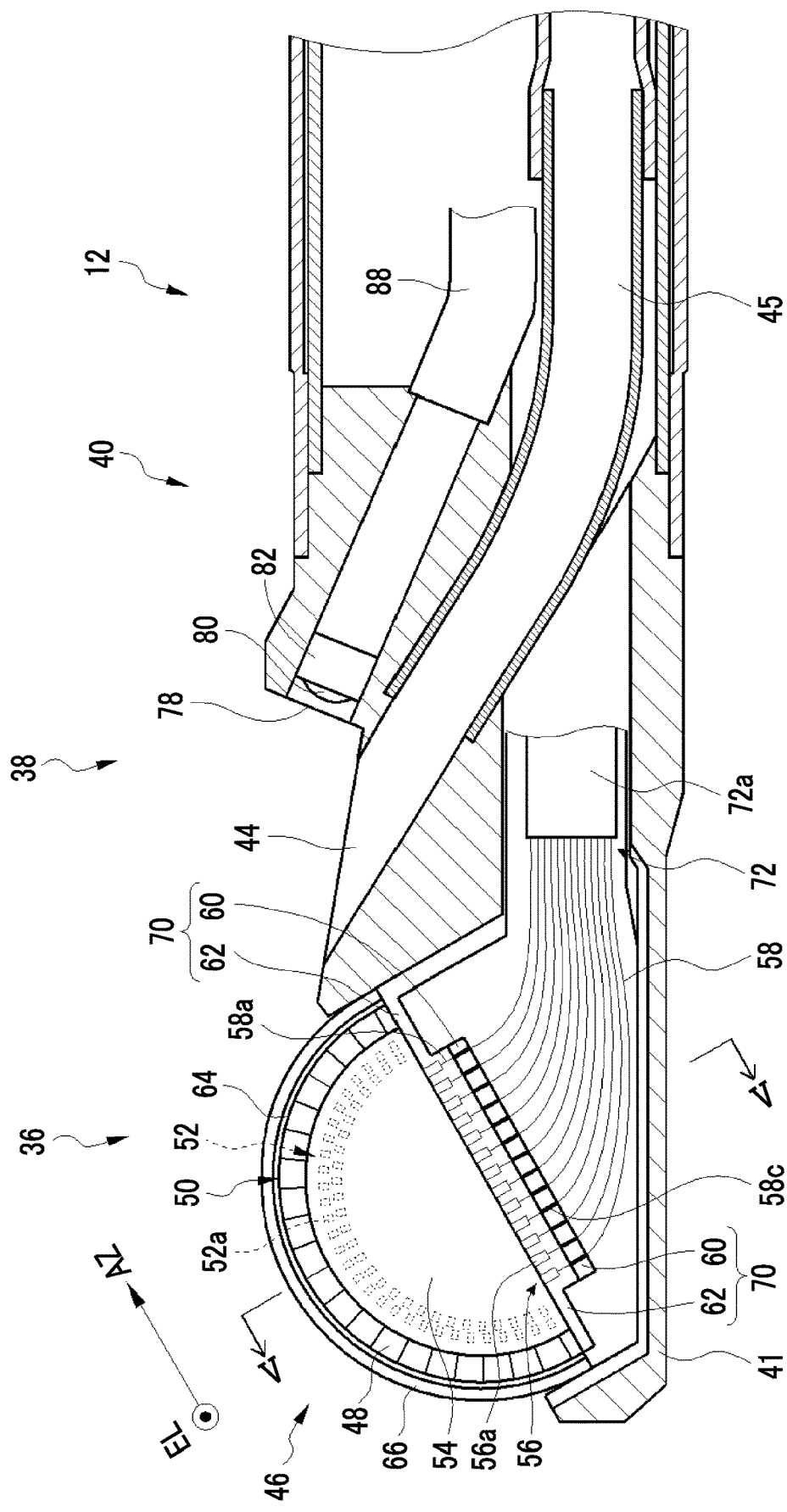
FIG. 3 is a view taken along line illustrated in FIG. 2 and seen from an arrow direction and is a partially longitudinal cross-sectional view schematically illustrating the distal end part of the ultrasonic endoscope illustrated in FIG. 2.

As illustrated in FIGS. 2 and 3, the distal end part 40 of the ultrasonic endoscope 12 is provided with the ultrasonic observation part 36 on a distal end side thereof for acquiring the ultrasound image, the endoscope observation part 38 on a proximal end side thereof for acquiring the endoscopic image, and a treatment tool delivery port 44 therebetween, and these are altogether attached to and held by a sheathing member 41 that serves as a distal end part body of the distal end part 40 of the ultrasonic endoscope 12 and is made of a rigid member, such as a hard resin.

In the example illustrated in FIG. 2, although the treatment tool delivery port 44 is provided between the ultrasonic observation part 36 and the endoscope observation part 38, the invention is not particularly limited to the illustrated example. The treatment tool delivery port 44 may be provided within the endoscope observation part 38 or may be provided closer to the proximal end side (bending part 42 side) than the endoscope observation part 38.

Figure 4:
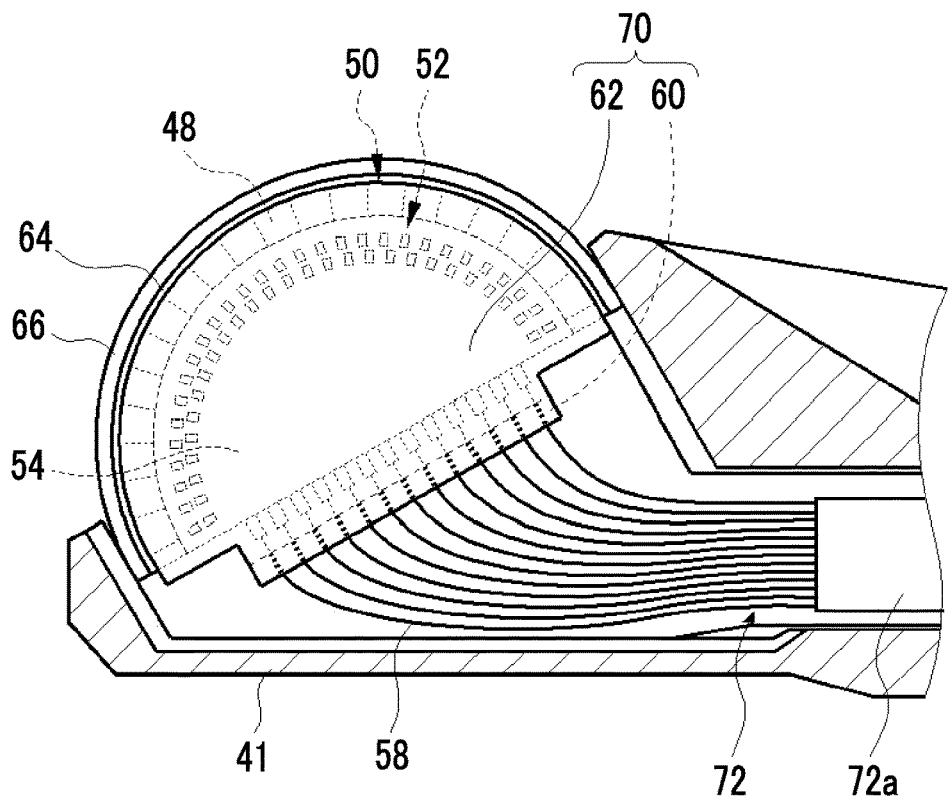
FIG. 4 is a partially enlarged cross-sectional view schematically illustrating an ultrasonic observation part of the distal end part of the ultrasonic endoscope illustrated in FIG. 2.
Figure 5:
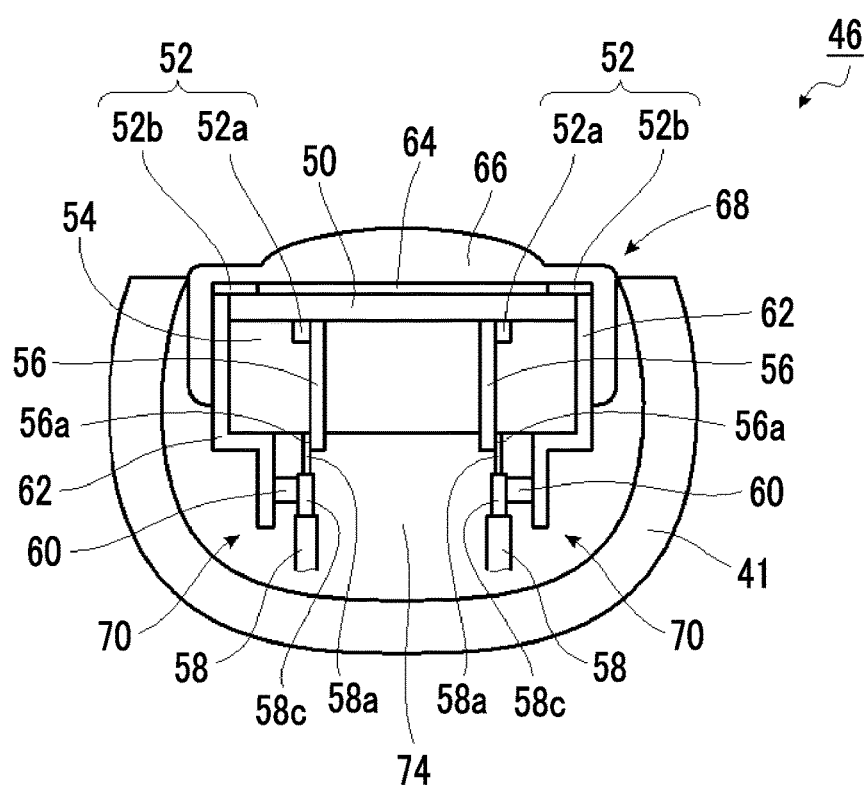
FIG. 5 is a view taken along line V-V illustrated in FIG. 3 and seen from an arrow direction and is a cross-sectional view of an example schematically illustrating the ultrasonic observation part of the distal end part of the ultrasonic endoscope illustrated in FIG. 3.

As illustrated in FIGS. 2 to 4, the ultrasonic observation part 36 is constituted of the ultrasonic oscillator unit 46 and the sheathing member 41 for attaching and holding the ultrasonic oscillator unit 46.

The ultrasonic oscillator unit 46 has the ultrasonic oscillator array 50 made of the plurality of ultrasonic oscillators (transducers) 48; an electrode part 52 including a plurality of individual electrodes 52a that are provided on an outer side surface or an inner side surface of the ultrasonic oscillator array 50 and are connected to the plurality of ultrasonic oscillators 48; a backing material layer 54 that supports the respective ultrasonic oscillators 48 of the ultrasonic oscillator array 50 from a lower surface side; a cable wiring part 56 including a plurality of connecting parts 56a that are electrically connected to the plurality of individual electrodes 52a of the electrode part 52, respectively, and wiring-connect signal lines 58a of a plurality of coaxial cables 58; a ground bar 60 that is disposed on the lower side of the backing material layer 54 opposite to the ultrasonic oscillator array 50 and has shield members 58c of the plurality of coaxial cables 58 connected thereto, respectively; and copper foil 62 that is pasted on the entire outer side surfaces of both of the plurality of ultrasonic oscillators 48 and the backing material layer 54, extends to the lower side of the backing material layer 54 opposite to the ultrasonic oscillator array 50, and is connected to the ground bar 60.

In the first embodiment of the invention, the ground bar 60 and the copper foil 62 are integrated with each other in advance, shield the plurality of ultrasonic oscillators 48, and constitute a heat dissipation structure 70, serving as a feature the invention, which dissipates the heat generated in the plurality of ultrasonic oscillators 48 and the backing material layer 54 to the shield members 58c of the plurality of coaxial cables 58. The details about the heat dissipation structure 70 will be described below.

In this way, the heat generated in the plurality of ultrasonic oscillators 48 and the backing material layer 54 is dissipated to the outside of the subject through the insertion part 22 via the shield members 58c of the plurality of coaxial cables 58 by the heat dissipation structure 70 serving as the feature of the invention.

Additionally, the ultrasonic oscillator unit 46 further has an acoustic matching layer 64 laminated on the ultrasonic oscillator array 50 and the acoustic lens 66 laminated on the acoustic matching layer 64. That is, the ultrasonic oscillator unit 46 includes a laminated body 68 of the acoustic lens 66, the acoustic matching layer 64, the ultrasonic oscillator array 50, and the backing material layer 54.

The acoustic matching layer 64 is a layer for matching the acoustic impedance between a subject, such as a human body, and the ultrasonic oscillators 48.

The acoustic lens 66 attached on the acoustic matching layer 64 is a lens for condensing the ultrasonic waves emitted from the ultrasonic oscillator array 50 toward the region to be observed. The acoustic lens 66 is made of, for example, silicon-based resin (millable type silicone rubber (HTV rubber), liquid silicone rubber (RTV rubber), or the like), butadiene-based resin, polyurethane-based resin, or the like. In order for the acoustic matching layer 64 to match the acoustic impedance between the subject and the ultrasonic oscillators 48 and increase the transmittance of the ultrasonic waves, powder, such as titanium oxide, alumina, or silica, is mixed with the acoustic lens 66 as needed.

The ultrasonic oscillator array 50 is an array of a plurality of channels, for example, 48 to 192 channels (CH) including a plurality of, for example, 48 to 192 rectangular parallelepiped-shaped ultrasonic oscillators (transducers) 48 that are arranged outward in a circular-arc shape.

That is, the ultrasonic oscillator array 50 is an array in which a plurality of ultrasonic oscillators 48 are arranged at a predetermined pitch in a one-dimensional array as in the illustrated example as an example. In this way, the respective ultrasonic oscillators 48 that constitute the ultrasonic oscillator array 50 are arranged at equal intervals in a convexly curved shape in an axis direction (the longitudinal axis direction of the insertion part 22) of the distal end part 40 and are sequentially driven on the basis of driving signals input from the ultrasonic wave processor device 14. Accordingly, convex electronic scanning is performed using a range where the ultrasonic oscillators 48 illustrated in FIG. 2 are arranged, as a scanning range.

Figure 11:
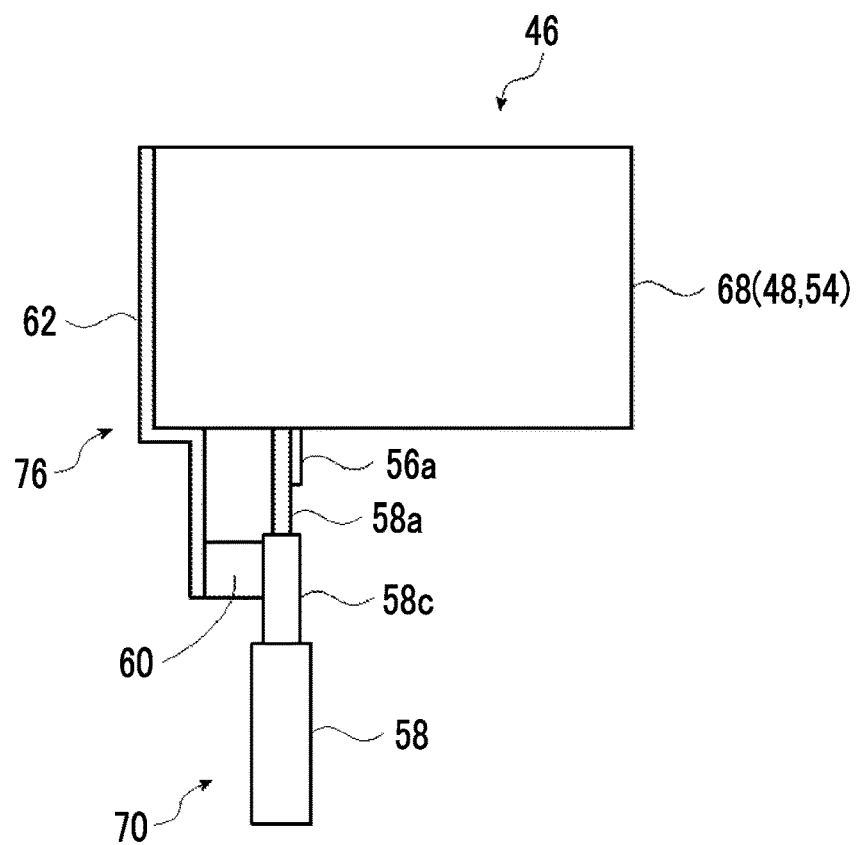
FIG. 11 is an explanatory view schematically illustrating a heat dissipation structure of an ultrasonic observation part of a distal end part of an ultrasonic endoscope of one embodiment of the invention.

The ultrasonic oscillator array 50 is disposed such that the length of the ultrasonic oscillators 48 in a longitudinal direction (EL (elevation) direction) orthogonal to an AZ direction (AZ (azimuth) direction) is shorter than that in a direction parallel to a bottom surface of the backing material layer 54 and a rear end side thereof is inclined so as to overhang. As illustrated in FIG. 11, the respective ultrasonic oscillators 48 has a configuration in which an electrode is formed on a bottom surface of, for example, a thick film of a piezoelectric body, such as PZT (lead zirconium titanate) or PVDF (polyvinylidene fluoride). One electrode is an individual electrodes 52a that is separately independent for each ultrasonic oscillators 48, and the other electrode is a common electrode (for example, a ground electrode) 52b common to all the ultrasonic oscillators 48. In the illustrated example, the plurality of individual electrodes 52a are respectively provided on inner lower surface sides of the plurality of ultrasonic oscillators 48, and are electrically connected to a plurality of wiring lines (not illustrated) of the cable wiring part 56, respectively. In addition, in the cable wiring part 56, the plurality of wiring lines (not illustrated) are electrically connected to the plurality of connecting parts 56a, respectively. Meanwhile, in the illustrated example, the common electrode 52b is provided on an upper surface of an end part of the ultrasonic oscillator 48, and is connected to the ground bar 60. The plurality of individual electrodes 52a and the common electrode 52b constitute the electrode part 52.

In addition, although illustration is omitted, a gap between two adjacent ultrasonic oscillator 48 is filled with a filler material, such as epoxy resin.

In the ultrasonic oscillator unit 46 of the ultrasonic observation part 36, in a case where each ultrasonic oscillators 48 of the ultrasonic oscillator array 50 is driven and a voltage is applied to both the electrodes of the ultrasonic oscillators 48, the piezoelectric bodies oscillate to sequentially generate the ultrasonic waves, and the ultrasonic waves are radiated toward the region to be observed of the subject. Then, by sequentially driving the plurality of ultrasonic oscillators 48 with an electronic switch, such as a multiplexer, scanning is performed with the ultrasonic waves within a scanning range along a curved surface on which the ultrasonic oscillator array 50 is disposed, for example, within a range of about several tens of mm from the center of curvature of the curved surface. As a result, in a case where the respective ultrasonic oscillators 48 of the ultrasonic oscillator array 50 generates heat in a case where ultrasonic waves are generated, and the backing material layer 54 also generates heat due to the action of the ultrasonic waves.

Additionally, in a case where the echo signals (ultrasound echoes) reflected from the region to be observed are received, the piezoelectric bodies oscillate to generate voltages, and the voltages are output to the ultrasonic wave processor device 14 as electrical signals (ultrasonic detection signals) according to the received ultrasound echoes. After various kinds of signal processing are performed in the ultrasonic wave processor device 14, the ultrasound image is displayed on the monitor 20.

As illustrated in FIGS. 3 and 4, the electrode part 52 is provided in a circular-arc shape on an inner lower surface (of the respective ultrasonic oscillators 48) of the ultrasonic oscillator array 50 perpendicular to a circular-arc surface resulting from the arrangement of the plurality of (48 to 192) ultrasonic oscillators 48, and includes the plurality of (48 to 192) individual electrodes 52*a* electrically connected to the plurality of (48 to 192) ultrasonic oscillators 48, respectively. In addition, the common electrode of the plurality of ultrasonic oscillators 48 may be included in the electrode part 52. In the invention, the "perpendicular" is not necessarily limited to 90 degrees, and includes substantially perpendicular, for example, 95 degrees±5 degrees, that is, an angle within a range of 85 degrees to 90 degrees.

In addition, in FIGS. 3 and 4, the plurality of individual electrodes 52*a* arranged in a circular-arc shape and the electrode part 52 including these electrodes are hidden under the backing material layer 54 and are not visible, but are indicated by dashed lines for easy understanding.

In the example illustrated in FIG. 5, electrode parts 52 are provided in two rows on the inner lower surface of the ultrasonic oscillator array 50 perpendicular to the arrangement surface of the plurality of ultrasonic oscillators 48. However, in a case where the number of ultrasonic oscillators 48 is small, an electrode part 52 may be provided in only one row. In a case where the plurality of ultrasonic oscillators 48 are arranged in a plurality of rows in a longitudinal direction, electrode parts 52 may be provided in a plurality of rows of two or more rows. In addition, electrode parts 52 may be respectively provided on both the outer side surfaces in the longitudinal direction of the ultrasonic oscillator array 50 as well as the inner lower surface of the ultrasonic oscillator array 50, or an electrode part 52 may be provided on one outer surface. Electrode parts 52 may be provided in one or more rows on the inner lower surface of the ultrasonic oscillator array 50 or may be provided on one outer side surface or both the outer side surfaces.

In addition, since it is preferable to the number of ultrasonic oscillators 48 is larger, it is preferable that the plurality of individual electrodes 52*a* are provided in a plurality of rows on the inner lower surface or on both the outer side surfaces of the ultrasonic oscillator array 50, or may be provided on both the inner lower surface and the outer side surfaces.

In addition, in the example illustrated in FIG. 5, the plurality of individual electrodes 52*a* are constituted of the individual electrodes provided on the end surface sides of the respective ultrasonic oscillators 48 in their longitudinal direction. However, the invention is not limited to this. As long as the individual electrodes 52*a* of the ultrasonic oscillators 48 are electrically connected, the individual electrodes 52*a* may be constituted of separate electrodes connected by wiring lines from the individual electrodes. Additionally, although the common electrode is directly included in the electrode part 52, an electrode connected by a wiring line from the common electrode 52*b* may be included.

It is preferable that the plurality of individual electrodes 52*a* and the common electrode 52*b* of the electrode part 52 are provided as electrode pads.

Next, as illustrated in FIGS. 3 and 5, the backing material layer 54 is a layer of a member that is made of a backing material disposed on an inside with respect to the arrangement surface of the plurality of ultrasonic oscillators 48, that is, a back surface (lower surface) of the ultrasonic oscillator array 50 and supports the plurality of ultrasonic oscillators 48 that are arranged in an array. A top surface (upper surface) of the backing material layer 54 is formed in a convex circular-arc cross-sectional shape.

In addition, in the example illustrated in FIG. 5, the backing material layer 54 has a configuration in which portions of the plurality of wiring lines (not illustrated) of the cable wiring part 56 connected to the plurality of individual electrodes 52*a* of the electrode part 52 are embedded therein. In addition, the plurality of connecting parts 56*a* of the cable wiring part 56 protrude downward from the backing material layer 54.

The backing material that constitutes the backing material layer 54 functions as a cushioning material that flexibly supports the respective ultrasonic oscillators 48 and the like of the ultrasonic oscillator array 50. For this reason, the backing material includes a material having rigidity, such as hard rubber, and an ultrasonic damping material (ferrite, ceramics, or the like) is added to the backing material as needed.

Hence, the ultrasonic oscillator array 50 is an array in which, in the illustrated example, the plurality of rectangular parallelepiped-shaped ultrasonic oscillators 48 are parallel to the longitudinal direction thereof, preferably, are arranged at equal intervals, on the circular-arc outer surface used as an upper surface of the backing material layer 54 formed in a covex circular-arc shape in cross-section, that is, an array in which the plurality of ultrasonic oscillators 48 are arranged outward in a circular-arc shape.

The cable wiring part 56 includes the plurality of wiring lines (not illustrated) electrically connected to the plurality of individual electrodes 52*a* of the electrode part 52, respectively, and the plurality of connecting parts 56*a* that are connected to the plurality of wiring lines (not illustrated), respectively, and wiring-connect the signal lines 58*a* of the plurality of coaxial cables 58. The cable wiring part 56 may include the plurality of connecting parts 56*a* at end parts of the plurality of wiring lines (not illustrated) electrically connected to the plurality of individual electrodes 52*a* of the electrode part 52.

However, from a viewpoint of easiness of connection to the plurality of individual electrodes 52*a* of the electrode part 52, it is preferable that the cable wiring part 56 is constituted of, for example, a wired board, such as a flexible printed wired board (hereafter simply referred to as a flexible printed circuit (FPC)), a printed wiring circuit board (hereinafter referred to as a printed circuit board (PCB)), or a printed wired board (hereinafter referred to as a PWB), and as illustrated in FIGS. 3 and 4, it is preferable that the cable wiring part 56 has a plurality of (48 to 192) wiring lines of for being electrically connected to the individual electrodes 52*a* of the plurality (48 to 192) of the electrode part 52, respectively, and the plurality of connecting parts 56a that are connected to the plurality of (48 to 192) of wiring lines, respectively.

In this case, the cable wiring part 56 may be constituted of one wired board, for example, a flexible wired board, such as the FPC, or a rigid wired board, such as the PCB or PWB, or may be constituted of a multilayer board in which the flexible wired board, such as the FPC, and the rigid wired board, such as the PCB or PWB, are integrated with each other. For example, as the cable wiring part 56, it is possible to use one in which an FPC having the plurality of (48 to 192) wiring lines for being electrically connected to the plurality of (48 to 192) individual electrodes 52a of the electrode part 52, and a rigid wired board having the plurality of (48 to 192) connecting parts 56a for wiring-connecting the signal lines 58a of the plurality of coaxial cables 58 are integrated with each other such that the plurality of (48 to 192) wiring lines and the plurality of (48 to 192) connecting parts 56a are respectively connected to each other.

In this way, the plurality of wiring lines of the cable wiring part 56 and the plurality of individual electrodes 52a of the electrode part 52 of the ultrasonic oscillator array 50 can be easily electrically connected to each other, respectively.

Here, the electrical connection between the plurality of wiring lines of the cable wiring part 56 and the plurality of individual electrodes (electrode pads) 52a of the electrode part 52 of the ultrasonic oscillator array 50 may be performed using an anisotropic conductive sheet or an anisotropic conductive paste or may be performed by heat fusion. In addition, this electrical connection is also necessarily limited to these connection methods, and any kind of method may be performed using as long as the workability of wiring is not hindered and the difficulty of the operation step does not become high, and well-known methods, such as soldering, may be used.

In this way, it is possible to provide the ultrasonic endoscope using the ultrasonic oscillator unit that can simplify ultrasonic oscillator wiring work, improve efficiency and improve workability, can be small-sized, has excellent workability in a case where the respective electrodes of the ultrasonic oscillator array and numerous cables are wired and low difficulty of the operation step, and has a wiring structure in which a load on a cable is unlikely to occur and there is less risk of disconnection.

Figure 6:
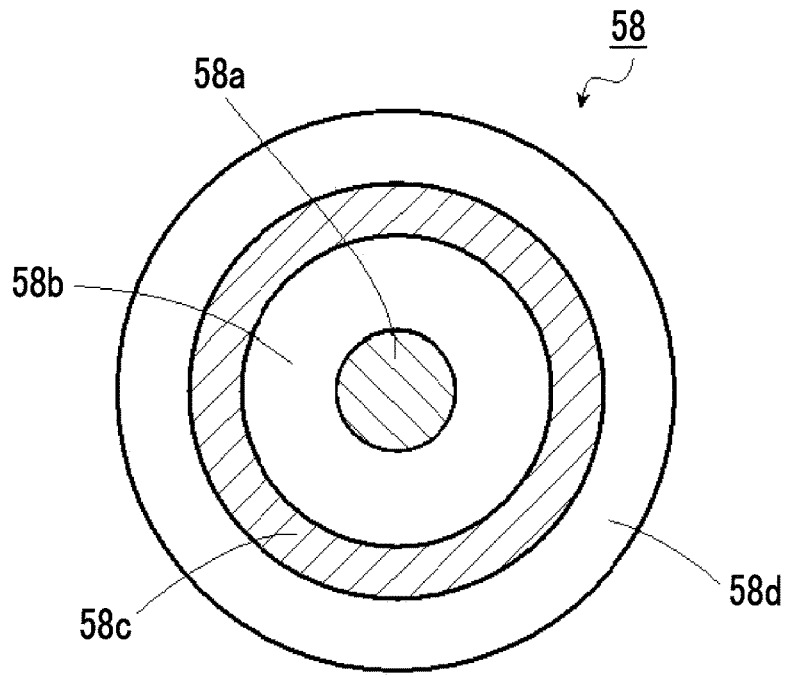
FIG. 6 is a cross-sectional view schematically illustrating the configuration of a coaxial cable used in the ultrasonic observation part of the distal end part of the ultrasonic endoscope illustrated in FIG. 3.

As illustrated in FIG. 6, each of the coaxial cables 58 used for the invention includes a signal line 58a at the center thereof, a first insulating layer 58b at an outer periphery of the signal line 58a, a shield member 58c at an outer periphery of the first insulating layer 58b, and a second insulating layer 58d at an outer periphery of the shield member 58c. In other words, the coaxial cable 58 is obtained by concentrically laminating the signal line 58a, the first insulating layer 58b, the shield member 58c, and the second insulating layer 58d from the center side.

Figure 7:
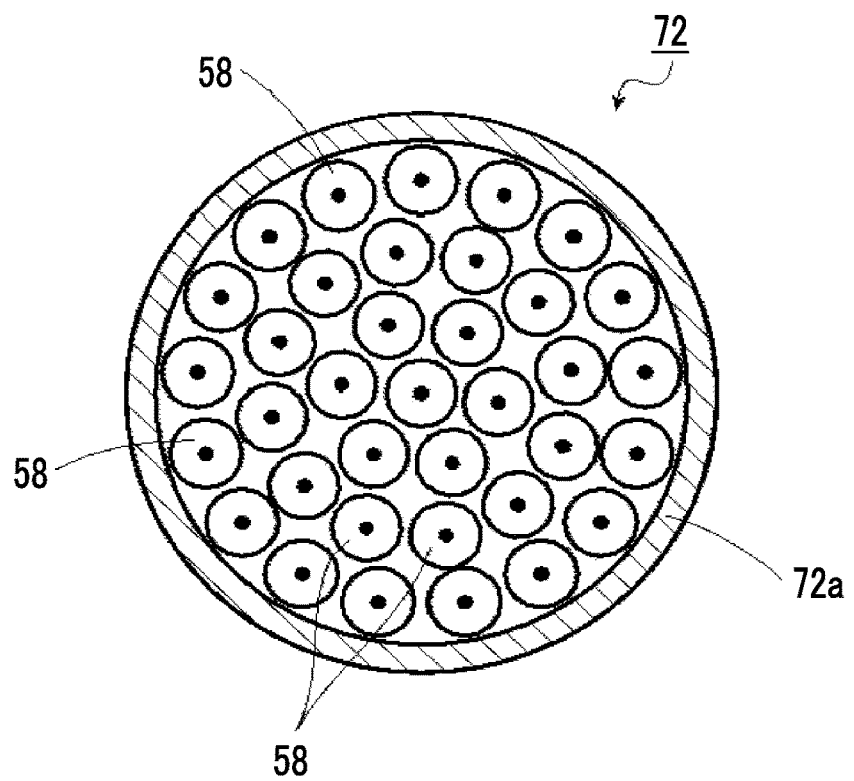
FIG. 7 is a cross-sectional view schematically illustrating a shielded cable constituted of a plurality of the coaxial cables used in the ultrasonic observation part of the distal end part of the ultrasonic endoscope illustrated in FIG. 3.

Here, in the invention, the plurality of coaxial cables 58 are used as one shielded cable 72 in which the plurality of coaxial cables 58 are wrapped with an outer sheath 72a at the outermost layer inside the outer sheath 72a, as illustrated in FIG. 7.

In addition, the shielded cable used for the invention is not limited to the shielded cable 72 in which the plurality of coaxial cables 58 are wrapped with the outer sheath 72a, and may be a non-coaxial cable formed as one cable unit in which a plurality of signal lines in which an outer periphery of a center conductor is wrapped with an insulating layer, such as a dielectric body, and a plurality of drain lines made of conductors functioning as the shield members are randomly and mixedly disposed, or may be a non-coaxial cable formed as one cable unit in which a plurality of signal lines in which an outer periphery of a center conductor is wrapped with an insulating layer, such as a dielectric body, is disposed on a center side, a plurality of outer conductors functioning as the shield members are disposed around the plurality of signal lines, and all the conductors are wrapped with a shielding material.

The ground bar 60 constitutes the heat dissipation structure 70, and is for electrically and thermally connecting the shield members 58c of the plurality of coaxial cables 58 of one shielded cable 72 to each other, as illustrated in FIG. 3.

Here, the "electrically connecting the two members, such as the ground bar 60 and the shield member 58c, to each other" means fixing the two members by direct contact or joining and fixing the two members with solder, a conductive adhesive, or the like such that an electric current flows well between the two members.

Additionally, the "thermally connecting the two members, such as the ground bar 60 and the shield member 58c, to each other" means fixing the two members by direct contact or joining and fixing the two members with solder, a heat conductive adhesive, or the like such that heat transfer occurs between the two members and heat is transferred from one member to the other member.

As the ground bar 60, any ground bars may be adopted as long as the plurality of shield members 58c of the plurality of coaxial cables 58 can be electrically connected to each other, for example, with solder or the like. Well-known related-art ground bars used for ultrasonic endoscopes may be adopted.

In addition, in electrically connecting the plurality of shield members 58c to the ground bar 60 and in electrically connecting the plurality of signal lines 58a to the plurality of connecting parts 56a of the cable wiring part 56, respectively, the outer sheath 72a on the distal end side of one shielded cable 72 is stripped and removed, the plurality of coaxial cables 58 are taken out, the second insulating layers 58d on the distal end side of the plurality of taken-out coaxial cables 58, the plurality of shield members 58c are stripped out to the outside, and the plurality of signal lines 58a are stripped out to the outside by leaving proximal end sides of the plurality of shield members 58c stripped out to the outside, cutting and removing distal end parts of the shield members 58c, and stripping and removing the second insulating layers 58d.

In this way, the plurality of shield members 58c of the plurality of coaxial cables 58 that are left as being stripped out to the outside are electrically connected to the ground bar 60 with solder or the like, respectively. Additionally, the plurality of signal lines 58a of the distal ends of the plurality of coaxial cables 58 that are stripped out to the outside are electrically connected to the plurality of connecting parts 56a of the cable wiring part 56 with solder or the like, respectively.

The copper foil 62 is disposed on outer side surfaces of the plurality of ultrasonic oscillators 48 of the ultrasonic oscillator array 50, and plays a role of a shielding effect and a heat dissipation effect. The copper foil 62 constitutes the heat dissipation structure 70 together with the ground bar 60, is pasted on the plurality of ultrasonic oscillators 48 of the ultrasonic oscillator array 50, and is disposed on a side surface of the ultrasonic oscillator array 50, that is, an outer side surface of the laminated body 68, specifically, at least on outer side surfaces of the ultrasonic oscillator array 50 and the backing material layer 54.

Here, in the heat dissipation structure 70 of the ultrasonic observation part 36 of the distal end part 40 of the ultrasonic endoscope 12 of the first embodiment of the invention, the copper foil 62 is used after being integrated with the ground bar 60 functioning as a second heat-conduction member of the invention in advance. However, in the invention, the copper foil 62 functions as a sheet-like first heat-conduction member of the invention that is disposed on the side surface of the ultrasonic oscillator array 50.

The copper foil 62 is not limited to the foil shape, and preferably has shapes, such as a mesh shape and a sheet shape, which can sufficiently conduct heat from side surfaces of the ultrasonic oscillator array 50 and the backing material layer 54, in the width direction.

In addition, the copper foil 62 is used as the sheet-like first heat-conduction member of the invention. However, the invention may not be limited to this. Any copper foil may be adopted as long as the copper foil has a thin plate-shaped body with excellent heat conductivity. For example, the copper foil may be metallic foils, such as silver foil, or may be thin metal sheets.

Meanwhile, the ground bar 60 functions as a ground part connected to the common electrode 52*b* of the electrode part 52 with respect to the signal lines 58*a* of the plurality of coaxial cables 58 electrically connected the plurality of individual electrodes 52*a* of the electrode part 52, respectively, and is electrically connected to the plurality of shield members 58*c* of the plurality of coaxial cables 58 to set the electric potential of the ground part to the electric potential of the plurality of shield members 58*c*.

In addition, since the ground bar 60, for example, is made of metal or the like and has electrical conductivity, the ground bar 60 also has heat conductivity. Hence, since the ground bar 60 is thermally and electrically connected to the copper foil 62 that is the first heat-conduction member of the invention, and the copper foil 62 is connected to the plurality of shield members 58*c*, the ground bar 60 also functions as the second heat-conduction member of the invention that thermally connect the copper foil 62, which is the first heat-conduction member of the invention, to the ground part.

Next, a method for manufacturing the ultrasonic endoscope of the first embodiment of the invention will be described. Here, although a manufacturing process of the heat dissipation structure 70 of the ultrasonic oscillator unit 46 of the ultrasonic observation part at the distal end part of the ultrasonic endoscope will be described in detail as the method for manufacturing the ultrasonic endoscope, respective constituent elements and respective members of the ultrasonic oscillator unit 46 are manufactured.

Additionally, although the method for manufacturing the ultrasonic endoscope 12 of the invention will be described with reference to FIGS. 8 to 11, FIGS. 8 to 11 are not views illustrating actual constituent elements and members but views for the description that only portions required for description are illustrated and portions that are not used for description are omitted.

In the ultrasonic endoscope of the first embodiment of the invention, as illustrated in schematic views in FIGS. 8 to 11, the heat dissipation structure 70 of the ultrasonic oscillator unit 46 of the ultrasonic observation part can be manufactured.

Figure 8:
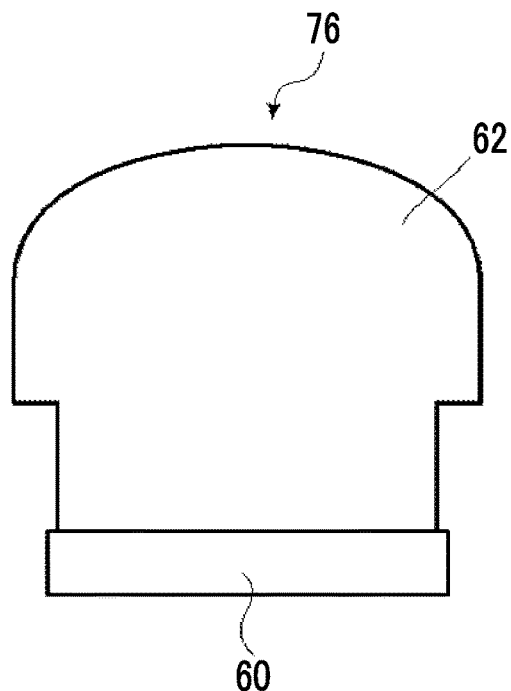
FIG. 8 is a schematic front view of an integrated member of copper foil and a ground bar in the ultrasonic observation part illustrated in FIG. 4.
Figure 9:
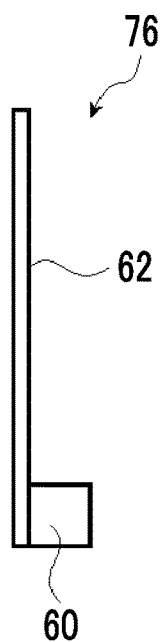
FIG. 9 is a schematic side view of the integrated member between the copper foil and the ground bar illustrated in FIG. 8.

First, as illustrated in FIGS. 8 and 9, the ground bar 60 is attached and connected to a lower side surface (in the drawing) of the copper foil 62 in advance and integrated therewith, and an integrated member 76 in which the copper foil 62 and the ground bar 60 are integrated with each other is prepared.

Figure 10:
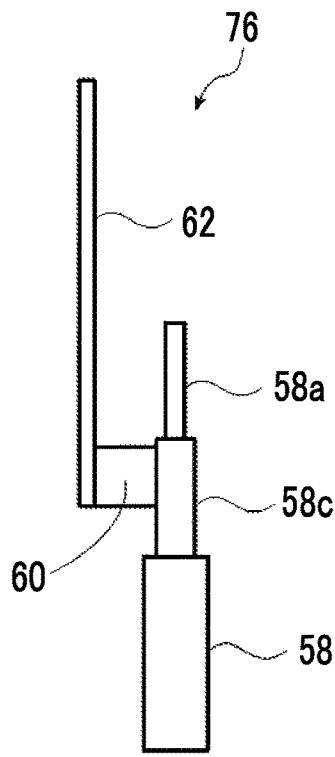
FIG. 10 is a side view schematically illustrating a connected state between the ground bar of the integrated member illustrated in FIG. 9, and a shield member of the coaxial cable.

Next, as illustrated in FIG. 10, the shield members 58*c* of the coaxial cables 58 are connected to the ground bar 60 of the integrated member 76 illustrated in FIGS. 8 and 9 with ordinary solder, for example, high-temperature solder used for ordinary solder connection, solder having a high melting point, or the like. In addition, although only one shield member 58*c* of one coaxial cable 58 connected to the ground bar 60 of the integrated member 76 is illustrated in FIG. 10, it is obvious that shield members 58*c* of the coaxial cables 58 of a number equivalent to a plurality of, that is, a required number of channels are connected to the ground bar 60 of the integrated member 76.

Next, as illustrated in FIG. 11, the signal lines 58*a* of the plurality of coaxial cables 58 in which the shield members 58*c* are connected to the ground bar 60 of the integrated member 76 are respectively connected to the corresponding connecting part 56*a* of the cable wiring part 56 with solder or the like, similarly to the case of the connection of the above-described shield members 58*c*. In addition, although not illustrated, the plurality of connecting parts 56*a* of the cable wiring part 56 are electrically connected to the plurality of corresponding individual electrodes 52*a* of the electrode part 52 of the ultrasonic oscillator array 50, respectively.

Additionally, simultaneously or before or after, the copper foil 62 of the integrated member 76 is pasted and disposed on outer side surfaces of the plurality of ultrasonic oscillators 48 of the backing material layer 54 and consequently on the outer side surface of the laminated body 68. In this case, it is preferable to bend the copper foil 62 at a portion abutting against a bottom surface of the backing material layer 54 of the laminated body 68 and dispose the copper foil 62 along the outer side surface of the laminated body 68. Additionally, it is preferable that the pasting of the copper foil 62 is performed using at least one conductive member, such as solder, silver paste, or a conductive adhesive, a silicon-based non-conductive adhesive, or the like.

In this way, the ultrasonic oscillator unit 46 of the ultrasonic endoscope 12 having the heat dissipation structure 70 can be manufactured.

In addition, in the ultrasonic oscillator unit 46 illustrated in FIG. 11, the heat dissipation structure 70 having the copper foil 62 is provided only on one outer side surface of both the outer side surfaces of the laminated body 68 (the plurality of ultrasonic oscillators 48 and the backing material layer 54). However, in the invention, as illustrated in FIG. 5, heat dissipation structures may be respectively provided on both the outer side surfaces of the laminated body 68. In addition, the ultrasonic endoscope 12 illustrated in FIG. 11 is schematically illustrated by simplifying the ultrasonic endoscope 12 illustrated in FIG. 5 in order to illustrate the heat dissipation structure 70 in an emphasized manner, and obviously has the same configuration as the ultrasonic endoscope 12 illustrated in FIG. 5 except that the heat dissipation structure 70 is provided on one side.

In the related art, in a case where the copper foil is connected to the ground bar to which that the plurality of coaxial cables are connected, and the copper foil and ground bar are solder-connected to each other using solder, there is a possibility that the signal lines of the coaxial cables may be damaged due to the heat of the solder and the signal lines may be damaged. However, in the ultrasonic endoscope 12 of the first embodiment, the copper foil 62 and the ground bar 60 are integrated with each other to form the integrated member 76, the shield members 58c of the plurality of coaxial cables 58 are connected to the ground bar 60 of the integrated member 76, then the signal lines 58a of the plurality of coaxial cables 58 are respectively connected to the plurality of connecting parts 56a of the cable wiring part 56, and the copper foil 62 of the integrated member 76 is disposed on the outer side surface of the laminated body 68. Thus, the heat dissipation structure 70 can be manufactured without performing solder connection using solder, and dissipation of heat from the ultrasonic oscillator 48 can be realized by the heat dissipation structure 70.

In this way, the ultrasonic endoscope of the invention can be reliably and stably manufactured without damaging the signal lines or the like connected to the constituent members, for example, ultra-compact ultrasonic oscillators and without causing an increase in cost.

Here, as illustrated in FIG. 5, in a case where the ultrasonic oscillator unit 46 is attached to the sheathing member 41 of the distal end part 40 of the ultrasonic endoscope 12 of the invention, it is preferable that a gap (space) between the backing material layer 54 of the laminated body 68 of the ultrasonic oscillator unit 46 and the cable wiring part 56, gaps (spaces) between the copper foil 62, the ground bar 60, and the plurality of coaxial cables 58 (the signal lines 58a, the shield members 58c, and the like), and gaps (spaces) between the laminated body 68, the copper foil 62, the ground bar 60, the plurality of coaxial cables 58, and the backing material layer 54, and the sheathing member 41 are filled with a filler material having excellent heat dissipation to form a filler layer 74.

Such a filler layer 74 is provided to fill the gap between the ultrasonic oscillator unit 46 and the sheathing member 41, particularly, the gap between the backing material layer 54 and the sheathing member 41, and can fix portions of wiring portions and extending portions of the cable wiring part 56 and the plurality of coaxial cables 58, thereby preventing occurrence of poor connection of the signal lines 58a of the coaxial cables 58 in the plurality of connecting parts 56a of the cable wiring part 56, occurrence of poor connection of the shield members 58c of the coaxial cables 58 in the ground bar 60, and disconnection of the coaxial cables 58 and the like. In this way, by covering the cable wiring part 56 and at least portions of the plurality of coaxial cables 58 with the filler material having excellent heat dissipation to form the filler layer 74, and portions of the plurality of coaxial cables 58 during the handling of an assembly of the ultrasonic oscillator unit 46 of the distal end part 40 of the ultrasonic endoscope 12 of the invention, and the ultrasonic observation part 36 can be protected.

Moreover, it is preferable that the acoustic impedances of the filler layer 74 and the backing material layer 54 are matched with each other such that the ultrasonic waves, which are oscillated from the ultrasonic oscillator array 50 and propagated to a lower side thereof, are not reflected at a boundary between the filler layer 74 and the backing material layer 54 and such that the ultrasonic waves oscillated from the ultrasonic oscillator array 50 can be reflected in an observation target or its peripheral part and can sufficiently damp the ultrasonic waves propagated to the lower side of the ultrasonic oscillator array 50. For that reason, in a case where the acoustic impedance of the filler layer 74 is defined as Zp (kg/m$^2$s) and the acoustic impedance of the backing material layer 54 is defined as Zb (kg/m$^2$s), it is preferable that an acoustic impedance reflectivity Q (%) of the filler layer 74 and the backing material layer 54 expressed by the following Equation (1) is 50% or less.

$$Q = 100 \times |Zp - Zb| / (Zp + Zb) \quad (1)$$

The acoustic impedance reflectivity Q is an index showing the easiness of reflection of the ultrasonic waves (acoustic beams) on a boundary surface between the filler layer 74 and the backing material layer 54, that is, shows that the acoustic impedance of the filler layer 74 and the acoustic impedance of the backing material layer 54 are matched with each other as the value thereof is closer to 0%. In a case where the above acoustic impedance reflectivity is about 50% or less, the noise caused by the ultrasonic waves propagated to the lower side of the ultrasonic oscillator array 50 can be processed so as not to become a problem in creating the ultrasound image in the ultrasonic wave processor device 14 using the ultrasonic signals received in the ultrasonic oscillator array 50.

Additionally, in a case where the ultrasonic waves are oscillated from the ultrasonic oscillator array 50 of the ultrasonic oscillator unit 46, the driving signals transmitted from the ultrasonic wave processor device 14 to the ultrasonic oscillator array 50 become thermal energy and the ultrasonic oscillator array 50 generates heat. Therefore, it is preferable that the filler layer 74 has heat dissipation. For that reason, it is preferable that the heat conductivity of the filler layer 74 is 1.0 W/m K or more.

The ultrasonic observation part 36 of the distal end part 40 of the ultrasonic endoscope 12 of the invention is configured as described above.

Next, the endoscope observation part 38 is constituted of an observation window 78, an objective lens 80, a solid-state imaging element 82, an illumination window 84, a washing nozzle 86, a wiring cable 88, and the like.

The distal end part 40 is detached obliquely upward of the observation window 78. The reflected light of the region to be observed, which has been incident from the observation window 78, is focused on an imaging surface of the solid-state imaging element 82 by the objective lens 80. The solid-state imaging element 82 photoelectrically converts of the reflected light of the region to be observed transmitted through the observation window 78 and the objective lens 80 and focused on the imaging surface, and outputs imaging signals. As the solid-state imaging element 82, a charge coupled device (CCD), a complementary metal oxide semiconductor (CMOS), or the like can be used. The captured image signals output by the solid-state imaging element 82 are transmitted to the endoscope processor device 16 by the universal cord 26 via the wiring cable 88 extending from the insertion part 22 to the operating part 24. The endoscope processor device 16 performs various kinds of signal processing and image processing with respect to the transmitted imaging signals, and displays the processed signals as the endoscopic optical image on the monitor 20.

Illumination windows 84 are provided on both sides with the observation window 78 interposed therebetween. An exit end of the light guide (not illustrated) is connected to the illumination windows 84. The light guide is provided to extend from the insertion part 22 to the operating part 24 and has an incident end connected to the light source device 18 connected via the universal cord 26. The illumination light emitted by the light source device 18 is transmitted to the light guide and is radiated from the illumination windows 84 to a region to be observed.

Additionally, the washing nozzle 86 jets air or washing water toward the observation window 78 and the illumination windows 84 through the air/water supply pipe line within the ultrasonic endoscope 12 from the water supply tank 21a in order to clean the surfaces of the observation window 78 and the illumination windows 84.

Additionally, the distal end part 40 is provided with the treatment tool delivery port 44. The treatment tool delivery port 44 is connected to a treatment tool channel 45 to be inserted through the inside of the insertion part 22, and a treatment tool inserted into a treatment tool insertion port 30 is introduced into the body cavity via the treatment tool channel 45 from the treatment tool delivery port 44. In addition, although the treatment tool delivery port 44 is located between the ultrasonic observation part 36 and the endoscope observation part 38, it is preferable to dispose the treatment tool delivery port 44 close to the ultrasonic observation part 36 in a case where it is configured that the movement of the treatment tool introduced into the body cavity from the treatment tool delivery port 44 is confirmed with the ultrasound image.

Although not illustrated, a rising stand that changes a delivery direction of the treatment tool introduced into the body cavity from the treatment tool delivery port 44 may be provided inside the treatment tool delivery port 44. A wire (not illustrated) is attached to the rising stand, the standing angle of the rising stand is changed by a push/pull operation resulting from the operation of a standing lever (not illustrated) of the operating part 24, and thereby the treatment tool is delivered in a desired direction.

In a case where the inside of the body cavity is observed by the ultrasonic endoscope 12, first, the insertion part 22 is inserted into the body cavity and searches for the region to be observed while the endoscopic optical image acquired in the endoscope observation part 38 is observed by the monitor 20.

Next, in a case where the distal end part 40 reaches the region to be observed and an instruction for acquiring the ultrasonic tomographic image is made, a driving control signal is input from the ultrasonic wave processor device 14 via the coaxial cables 58 within the ultrasonic endoscope 12, the cable wiring part 56, and the electrode part 52 to the ultrasonic oscillators 48. In a case where the driving control signal is input, a regular voltage is applied to both the electrodes of each ultrasonic oscillators 48. Then, the piezoelectric bodies of the ultrasonic oscillators 48 are excited, and the ultrasonic waves are emitted to the region to be observed via the acoustic lens 66.

In addition, in this case, the ultrasonic oscillator 48 and the backing material layer 54 generate heat. However, the generated heat is efficiently transferred to the copper foil 62 that constitutes the heat dissipation structure 70. The heat conducted through the copper foil 62 is efficiently transferred to the shield members 58c of the plurality of coaxial cables 58 via the ground bar 60 integrally connected to the copper foil 62 and is efficiently dissipated to the outside of the body cavity of the subject. Thus, since the temperature rise of the distal end part 40 of the ultrasonic endoscope 12 is suppressed, there is no possibility of damage, such as low-temperature burn, to a body cavity surface that comes into contact with the distal end part 40.

After the ultrasonic waves are radiated as described above, the echo signals from the region to be observed are received by the ultrasonic oscillator 48. The radiation of the ultrasonic waves and the reception of the echo signals are repeatedly performed while the ultrasonic oscillators 48 to be driven are shifted by the electronic switch, such as the multiplexer. Accordingly, the region to be observed is scanned with the ultrasonic waves. In the ultrasonic wave processor device 14, the ultrasonic tomographic image is created on the basis of the detection signals output from the ultrasonic oscillators 48 upon receiving the echo signals. The created ultrasonic tomographic image is displayed on the monitor 20.

The ultrasonic endoscope of the first embodiment of the invention is basically configured as described above.

Hereinbelow, ultrasonic endoscopes and methods for manufacturing the ultrasonic endoscopes in second to fourth embodiments of the invention will be described with reference to FIGS. 12 to 19. Here, similarly to FIGS. 8 to 11, FIGS. 12 to 19 are views schematically illustrating detailed structures of ultrasonic oscillator units in a simplified manner in order to illustrate heat dissipation structures of the ultrasonic oscillator units of ultrasonic observation parts of distal end parts of the ultrasonic endoscope, and are not views illustrating actual constituent elements and members but views for the description that only portions required for description are illustrated and portions that are not used for description are omitted.

Second Embodiment

Figure 12:
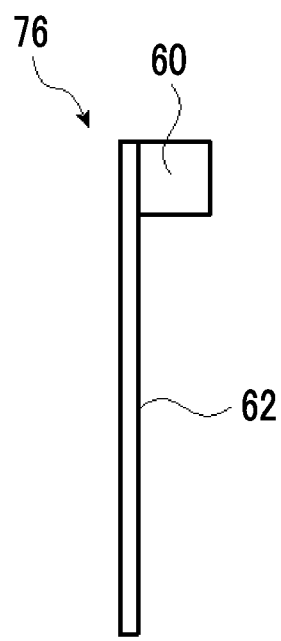
FIG. 12 is a schematic side view of another forms of the integrated member illustrated in FIG. 9.
Figure 13:
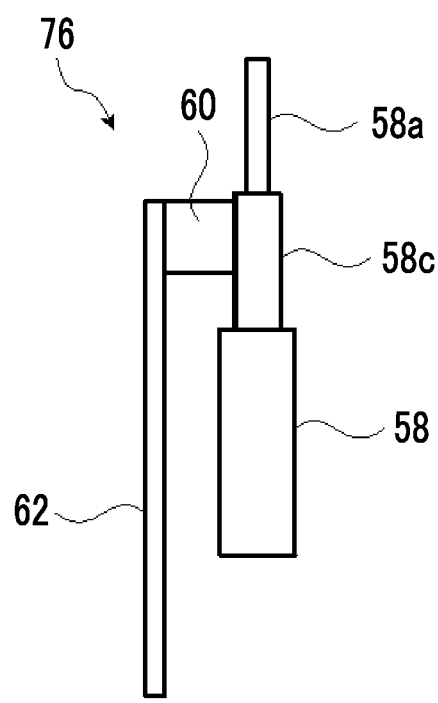
FIG. 13 is a side view schematically illustrating a connected state between the ground bar of the integrated member illustrated in FIG. 12, and the shield member of the coaxial cable.
Figure 14:
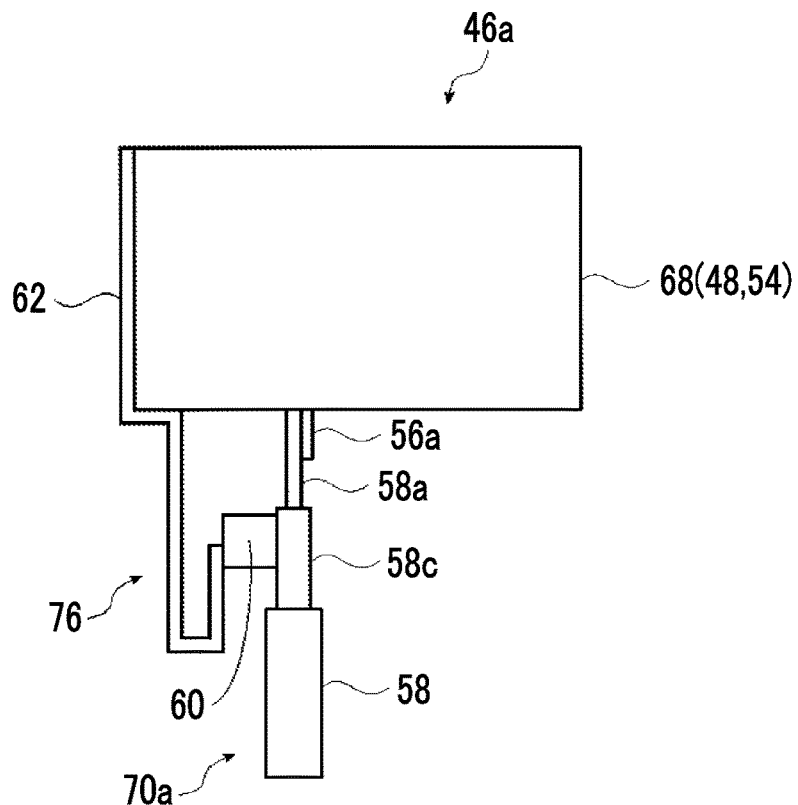
FIG. 14 is an explanatory view schematically illustrating a heat dissipation structure of an ultrasonic endoscope of another embodiment of the invention.

FIGS. 12 and 13 are schematic views illustrating a manufacturing process of a heat dissipation structure of an ultrasonic oscillator unit of an ultrasonic endoscope related to a second embodiment of the invention, and FIG. 14 is an explanatory view schematically illustrating the heat dissipation structure of the ultrasonic oscillator unit of the ultrasonic endoscope related to the second embodiment of the invention.

In the ultrasonic endoscope of the second embodiment of the invention, as illustrated in schematic views in FIGS. 12 to 14, a heat dissipation structure 70a of an ultrasonic oscillator unit 46a can be manufactured.

First, the ground bar 60 is attached and connected to the lower side surface (in the drawing) of the copper foil 62 in advance and integrated therewith, and the integrated member 76 (illustrated in FIG. 9) in which the copper foil 62 and the ground bar 60 are integrated with each other is prepared. Then, as illustrated in FIG. 12, the copper foil 62 and the ground bar 60 are inverted, and the copper foil 62 is pulled out to a side opposite to the ultrasonic oscillator 48.

Next, as illustrated in FIG. 13, the shield members 58c of the plurality of coaxial cables 58 are connected to the ground bar 60 of the integrated member 76 illustrated in FIG. 12 with ordinary solder.

Next, as illustrated in FIG. 11, the signal lines 58a of the plurality of coaxial cables 58 to which the shield members 58c are connected to the ground bar 60 of the integrated member 76 are respectively connected to the connecting parts 56a of the cable wiring part 56 electrically connected to the plurality of corresponding individual electrodes 52a of the electrode part 52 of the ultrasonic oscillator array 50 with ordinary solder or the like.

Thereafter, it is possible to manufacture the ultrasonic oscillator unit 46a of the ultrasonic endoscope of the present embodiment having the heat dissipation structure 70a having a structure in which the copper foil 62 is folded by pulling out the copper foil 62 to the side of the integrated member 76 opposite to the ultrasonic oscillator 48 to the ultrasonic oscillator 48 side and pasting and disposing the copper foil 62 on the outer side surface of the laminated body 68 (the plurality of ultrasonic oscillators 48 and the backing material layer 54). That is, the heat dissipation structure 70a of the ultrasonic oscillator unit 46a of the ultrasonic endoscope of the present embodiment is different from the heat dissipation structure 70 of the ultrasonic oscillator unit 46 illustrated in FIG. 11 only in the structure in which the copper foil 62 is folded.

The heat dissipation structure 70a of the present embodiment has the structure in which the copper foil 62 is folded. Thus, with respect to the heat dissipation structure 70 of the first embodiment, wiring space can be made small, and it is possible to save the space. In addition, also in the ultrasonic oscillator unit 46a of the present embodiment, similarly to the ultrasonic oscillator unit 46 of the first embodiment, it is obvious that heat dissipation structures 70a may be provided on both the outer side surfaces of the laminated body 68 as well on one outer side surface of the laminated body 68.

Third Embodiment

In the above-described first and second embodiments, the copper foil and the ground bar are integrated with each other in advance. However, the invention is not limited to this and the copper foil and the ground bar may not be integrated with each other in advance.

Figure 15:
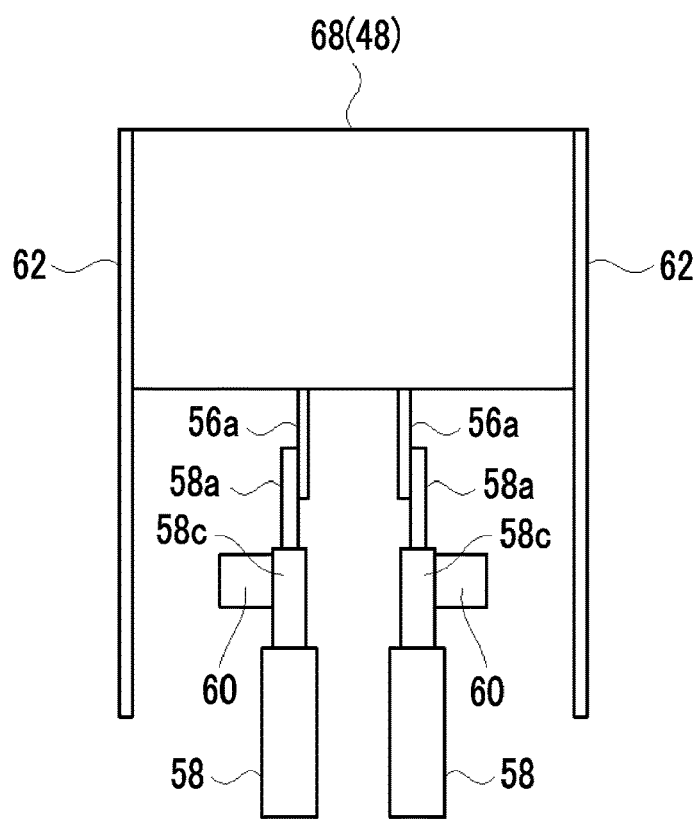
FIG. 15 is an explanatory view schematically illustrating one manufacturing process of a heat dissipation structure of an ultrasonic endoscope of still another embodiment of the invention.
Figure 16:
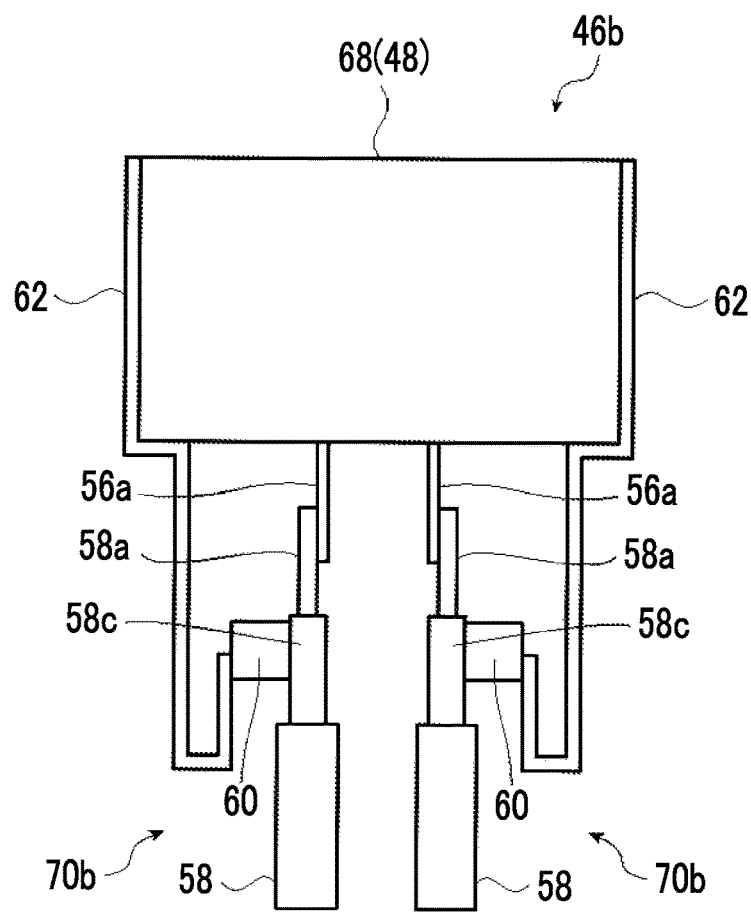
FIG. 16 is an explanatory view schematically illustrating the heat dissipation structure of the ultrasonic endoscope of the still other embodiment of the invention.

FIG. 15 is a schematic view illustrating a manufacturing process of a heat dissipation structure of an ultrasonic oscillator unit of an ultrasonic endoscope related to a third embodiment of the invention, and FIG. 16 is an explanatory view schematically illustrating the heat dissipation structure of the ultrasonic oscillator unit of the ultrasonic endoscope related to the third embodiment of the invention.

As illustrated in FIG. 15, the shield members 58c of the plurality of coaxial cables 58 are connected to the ground bar 60 with ordinary solder or the like in advance, the signal lines 58a of the plurality of coaxial cables 58 are respectively connected to the connecting parts 56a of the cable wiring part 56 electrically connected to the plurality of corresponding individual electrodes 52a of the electrode part 52 of the ultrasonic oscillator array 50 with ordinary solder or the like.

Additionally, the copper foil 62 is pasted and disposed on the outer side surface of the laminated body 68 (the plurality of ultrasonic oscillators 48 and the backing material layer 54).

Thereafter, as illustrated in FIG. 16, the copper foil 62 is folded and is connected to the ground bar 60 using at least one of low-temperature solder, which can be solder-connected at a temperature lower than ordinary solder or the like, solder with a low melting point, silver paste, and a conductive adhesive.

In this way, an ultrasonic oscillator unit 46b of the ultrasonic endoscope of the present embodiment having the heat dissipation structure 70b of the present embodiment can be manufactured.

In addition, in the ultrasonic oscillator unit 46b of the present embodiment, it is obvious that the heat dissipation structure 70b may be provided on one outer side surface of the laminated body 68 as well as on both the outer side surfaces of the laminated body 68.

Additionally, in the heat dissipation structure 70b of the present embodiment, the ground bar 60 and the copper foil 62 are not integrated with each other. Thus, it is necessary to connect the ground bar 60 and the copper foil 62 to each other after the signal lines 58a are connected to the connecting parts 56a of the cable wiring part 56 with ordinary solder or the like. However, since the low-temperature solder that can be solder-connected at a temperature lower than the ordinary solder or the like is used for the connection between the ground bar 60 and the copper foil 62, damage to the signal lines 58a can be eliminated similarly to the first and second embodiments.

Fourth Embodiment

Figure 17:
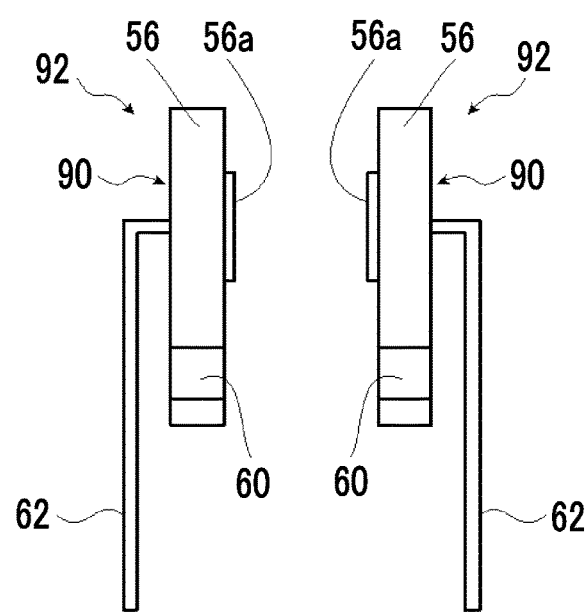
FIG. 17 is an explanatory view schematically illustrating one manufacturing process of a heat dissipation structure of an ultrasonic endoscope of a still further embodiment of the invention.
Figure 18:
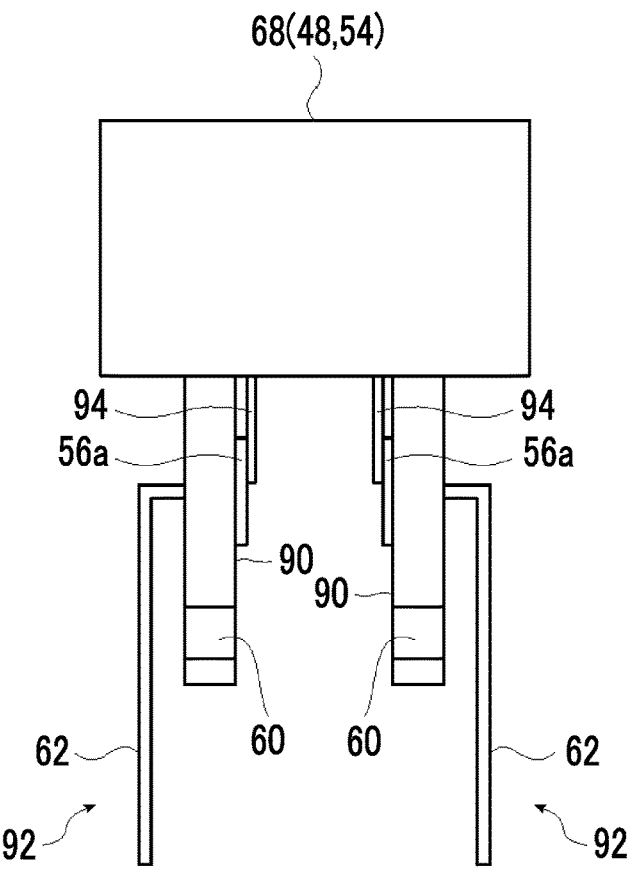
FIG. 18 is an explanatory view schematically illustrating another manufacturing process of the heat dissipation structure of the ultrasonic endoscope of the still further embodiment of the invention.
Figure 19:
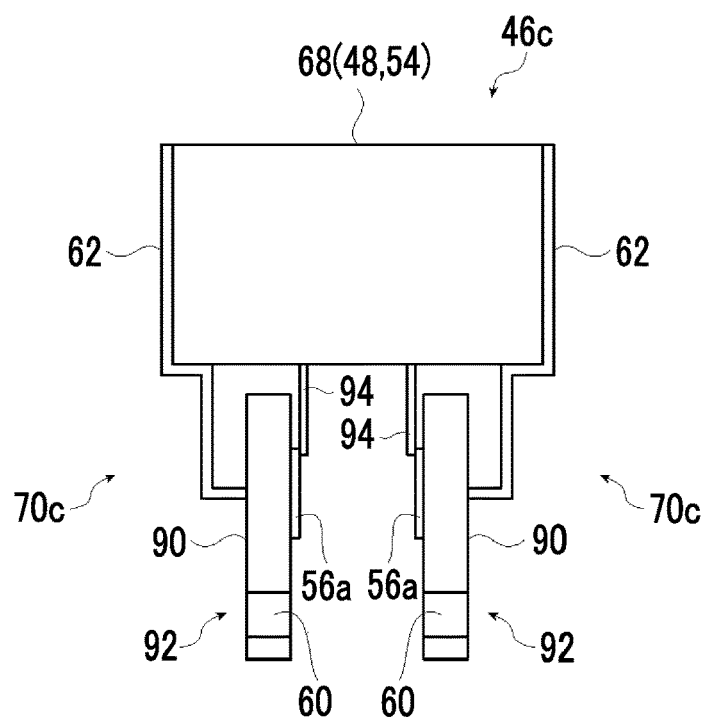
FIG. 19 is an explanatory view schematically illustrating the heat dissipation structure of the ultrasonic endoscope of the still further embodiment of the invention.

FIGS. 17 and 18 are schematic views illustrating a manufacturing process of a heat dissipation structure of an ultrasonic oscillator unit of an ultrasonic endoscope related to a fourth embodiment of the invention, and FIG. 19 is an explanatory view schematically illustrating the heat dissipation structure of the ultrasonic oscillator unit of the ultrasonic endoscope related to the fourth embodiment of the invention.

First, a heat dissipation structure 70c of an ultrasonic oscillator unit 46c of the ultrasonic endoscope related to the present embodiment illustrated in FIG. 19 are different from the heat dissipation structures of the first to third embodiments in that a wired board 90 including a portion serving as the ground bar 60, and a portion serving as the cable wiring part 56 having the plurality of connecting parts 56a to which the signal lines 58a of the plurality of coaxial cables 58 are connected, and can improve the workability of connection with the individual electrodes 52a of the plurality of ultrasonic oscillators 48 of the electrode part 52 of the ultrasonic oscillator array 50.

As illustrated in FIG. 17, the wired board 90 including the portion serving as the ground bar 60 is prepared, and the copper foil 62 is electrically connected to the ground bar 60 so as to be pulled out to a lower side (in the drawing) opposite to a side where the ultrasonic oscillator array 50 is disposed. In this case, since a connecting part of the copper foil 62 to the wired board 90 does not need to be directly connected to the ground bar 60 and may be electrically joined to the ground bar 60, the degree of freedom of the layout of the copper foil 62 can be improved. In the illustrated example, the copper foil 62 is connected to the position on the wired board 90 separated from the ground bar 60.

Here, as the wired board 90, the above-described flexible wired board, such as the FPC, may be used, and the rigid wired board, such as the PCB or PWB, may be used.

In the example illustrated in FIG. 17, a pair of (two) integrated members 92 in which the copper foil 62 and the wired board 90 are integrated with each other are prepared in advance.

Next, as illustrated in FIG. 18, the plurality of connecting parts 56a of the wired boards 90 of the pair of (two) integrated members 92 are connected to the plurality of wiring lines 94 connected to the corresponding individual electrodes 52a of the plurality of ultrasonic oscillators 48 of the electrode part 52 of the ultrasonic oscillator array 50.

Next, as illustrated in FIG. 19, it is possible to manufacture the ultrasonic oscillator unit 46c of the ultrasonic endoscope of the present embodiment having the heat dissipation structure 70c having a structure in which the copper foil 62 is folded by pulling out the copper foil 62 to the side of the integrated member 92 opposite to the ultrasonic oscillator 48 to the ultrasonic oscillator 48 side and pasting and disposing the copper foil 62 on the outer side surface of the laminated body 68 (the plurality of ultrasonic oscillators 48 and the backing material layer 54).

In addition, although not illustrated in the heat dissipation structure 70c illustrated in FIG. 19, it is obvious that the shield members 58c of the plurality of coaxial cables 58 are connected to the ground bar 60 of the integrated member 92 with ordinary solder or the like, and the signal lines 58a of the plurality of coaxial cables 58 are respectively connected to the plurality of connecting parts 56a provided at the cable wiring part 56 of the integrated member 92 with the ordinary solder or the like.

Additionally, also in the ultrasonic oscillator unit 46c of the present embodiment, it is obvious that the heat dissipation structure 70c may be provided on one outer side surface of the laminated body 68 as well as on both the outer side surfaces of the laminated body 68.

Additionally, although the integrated member 92 in which the copper foil 62 and the wired board 90 are integrated with each other in advance is used in the example illustrated in FIGS. 17 to 19, the present embodiment is not limited to this. The copper foil 62 may be connected to the wired board 90 after the plurality of connecting parts 56a of the wired board 90 are respectively to the plurality of wiring lines 94. Moreover, the copper foil 62 may be connected to the wired board 90 after the signal lines 58a of the plurality of coaxial cables 58 are respectively connected to the plurality of connecting parts 56a, and/or after the shield members 58c of the plurality of coaxial cables 58 are connected to the ground bar 60.

Fifth Embodiment

Figure 20:
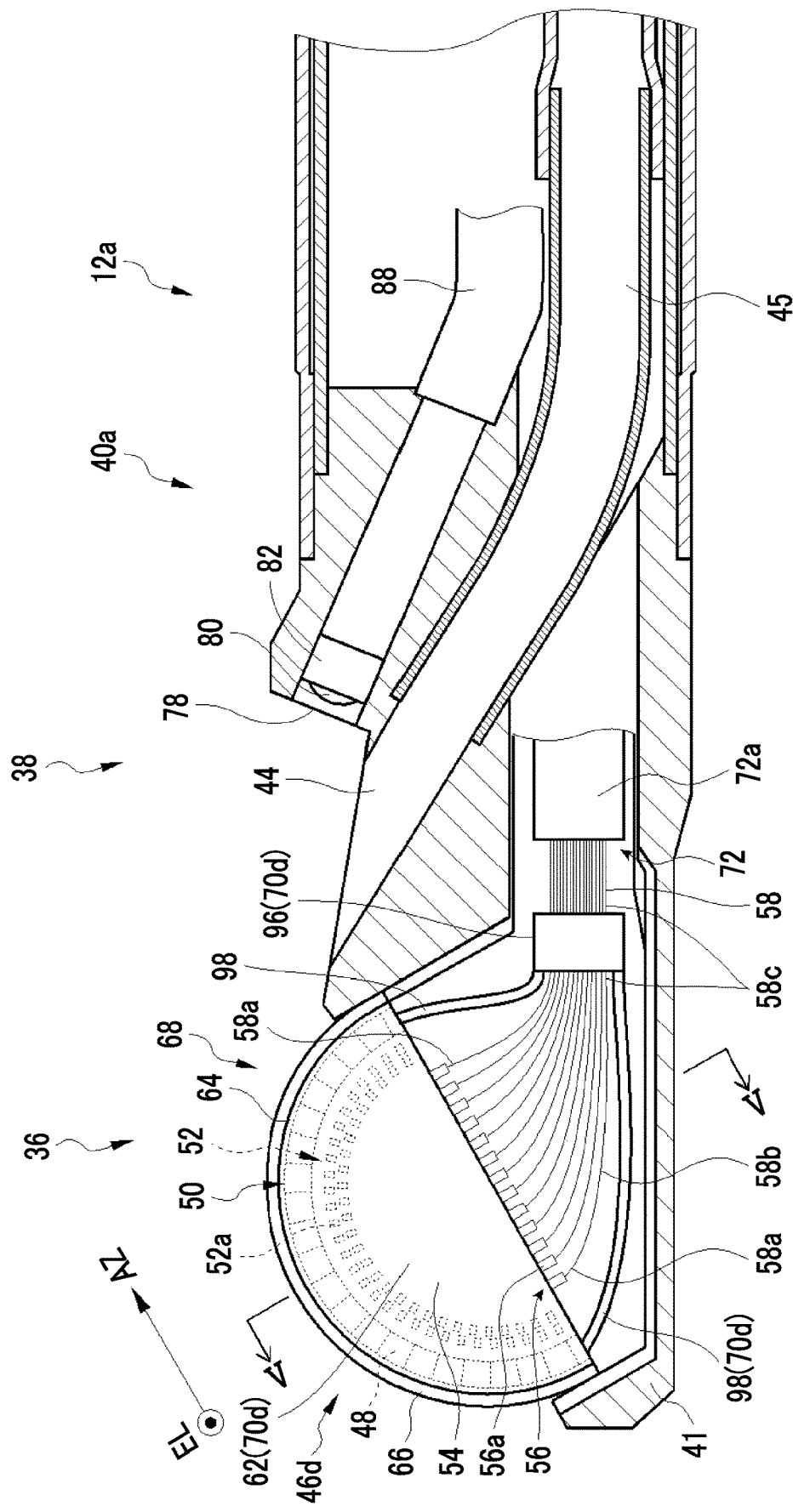
FIG. 20 is a partially cross-sectional view schematically illustrating a distal end part of an ultrasonic endoscope of a still further embodiment of the invention.

FIG. 20 is a partially cross-sectional view schematically illustrating a distal end part of an ultrasonic endoscope related to a fifth embodiment of the invention.

A distal end part 40a of an ultrasonic endoscope 12a illustrated in FIG. 20 has the same configuration as the distal end part 40 of the ultrasonic endoscope 12 illustrated in FIGS. 3 and 4 except for being different therefrom in that a collective ground 96 is provided instead of the ground bar 60 and the copper foil 62 disposed on the outer side surface of the laminated body 68 (the plurality of ultrasonic oscillators 48 and the backing material layer 54) is thermally connected to the collective ground 96 via a second heat-conduction member 98. Thus, the same constituent elements will be designated by the same reference signs, and the description thereof will be omitted.

A heat dissipation structure 70d of an ultrasonic oscillator unit 46d of the distal end part 40a of the ultrasonic endoscope 12a illustrated in FIG. 20 includes the collective ground 96 serving as the ground part of the invention, the copper foil 62 that is the first heat-conduction member of the invention, and the second heat-conduction member 98 to which the copper foil 62 is thermally connected to the collective ground 96.

The collective ground 96 brings the shield members 58c of the plurality of coaxial cables 58 of the shielded cable 72 into close contact with each other, and binds the shield members 58c into a metallic rhomboid, and all the shield members 58c and the metallic rhomboid are electrically and thermally connected to each other.

In addition, in the collective ground 96, the shield members 58c of the plurality of coaxial cables 58 including the front and the rear of the collective ground 96 serve as outer surfaces, and distal ends of the plurality of coaxial cables 58 connected to the plurality of connecting parts 56a of the cable wiring part 56 are only the signal lines 58a. Between the collective ground 96 and the plurality of connecting parts 56a, the first insulating layer 58b serves as an outer surface, the signal lines 58a are covered with the first insulating layer 58b, and the plurality of signal lines 58a are insulated from each other.

As long as the heat generated in the plurality of ultrasonic oscillators 48 and the backing material layer 54 and trans-ferred to the copper foil 62 can be conducted to the collective ground 96, the second heat-conduction member 98 is not particularly limited. Any second heat-conduction member may be adopted as long as the second heat-conduction member has heat conductivity and is capable of being flexibly housed in a narrow space of the distal end part 40a of the ultrasonic endoscope 12a. As the second heat-conduction member 98, it is necessary to have heat conductivity and be capable of being flexibly housed in a narrow space. Thus, the second heat-conduction member 98 may include, for example, a heat conductive cable, such as a cable including a core wire, a heat conductive wire, such as a metal wire, a heat conductive net, such as a metal net member, one obtained by extending a portion of the copper foil 62, which is the first heat-conduction member, as a wire.

In a case where these heat-conduction members are used as the second heat-conduction member 98, in order to improve heat transfer efficiency, it is preferable to use a cable including a core wire thicker than the signal lines 58a of the coaxial cables 58 or a metal wire thicker than the signal lines 58a.

Additionally, in a case where flexibility capable of being housed in a narrow space is required as the second heat-conduction member 98, it is preferable to use a metal-braided net member.

Moreover, noise tolerance can be improved by using an insulating heat-conduction member as the second heat-conduction member 98. As the insulating heat-conduction member, for example, heat dissipation silicone rubber, a heat dissipation sheet, or the like can be used.

All the ultrasonic endoscopes each including a heat dissipation structure at a distal end part thereof in the first to fifth embodiments of the invention as described above are convex ultrasonic endoscopes each having a convex ultrasound probe. However, the invention is not limited to this, and radial ultrasonic endoscopes having a radial ultrasound probe including a heat dissipation structure at a distal end part thereof may be adopted.

Sixth Embodiment

FIG. 21 is a partially enlarged plan view schematically illustrating a distal end part of an insertion part of an ultrasonic endoscope of the present embodiment. Additionally, FIG. 22 is a view taken along line X-X illustrated in FIG. 21 and seen from an arrow direction and is a partially longitudinal cross-sectional view of the distal end part of the insertion part of the ultrasonic endoscope illustrated in FIG. 21.

In addition, an ultrasonic endoscope 100 of the sixth embodiment illustrated in FIGS. 21 and 22 has the same configuration as the ultrasonic endoscope 12 of the first embodiment illustrated in FIGS. 1 to 7 except for being different therefrom in that a distal end part 102 including a radial ultrasonic observation part 104 and a radial endoscope observation part 106 are provided instead of the distal end part 40 including the convex ultrasonic observation part 36 and the convex endoscope observation part 38. Thus, the same constituent elements will be designated by the same reference signs, and the description thereof will be omitted.

As illustrated in FIGS. 21 and 22, the ultrasonic endoscope 100 of the present embodiment has the distal end part 102 including the radial ultrasonic observation part 104 and the radial endoscope observation part 106, and images the inside of the body cavity of the subject to acquire the ultrasound image (echo signals) and the endoscopic image (image signals), respectively. The ultrasonic endoscope 100 has an insertion part (22) including a bending part (42) and a flexible part (43), an operating part (24), and a universal cord (26), though not illustrated in FIGS. 21 and 22, similarly to the ultrasonic endoscope 12 illustrated in FIG. 1, in addition to the distal end part 102.

Here, in the example illustrated in FIGS. 21 and 22, the ultrasonic observation part 104 is disposed closer to a distal end side of the ultrasonic endoscope 100 than the endoscope observation part 106. However, the invention is not limited to this. The ultrasonic observation part 104 may be disposed closer to a proximal end side than the endoscope observation part 106, or may be disposed closer to the distal end side than some constituent elements of the endoscope observation part 106 and closer to the proximal end side than the remaining constituent elements.

In addition, the ultrasonic endoscope 100 of the present embodiment may include a mechanism that delivers treatment tools, such as forceps, a puncturing needle, and a high-frequency knife, similarly to the ultrasonic endoscope 12 of the first embodiment illustrated in FIGS. 1 to 7. A treatment tool delivery port (44 (refer to FIG. 3)) that allows the treatment tools to be delivered therethrough may be disposed closer to the proximal end side than the ultrasonic observation part 104, for example, between the ultrasonic observation part 104 and the endoscope observation part 106, or may be disposed on the distal end side, for example, the foremost end of the ultrasonic endoscope 100.

Additionally, the endoscope observation part 106 of the ultrasonic endoscope 100 of the present embodiment has the same configuration as the endoscope observation part 38 of the ultrasonic endoscope 12 of the first embodiment illustrated in FIGS. 2 and 3, and obviously has an observation part (78), an objective lens (80), a solid-state imaging element (82), an illumination window (84), a washing nozzle (86), a wiring cable (88), and the like.

As illustrated in FIGS. 21 and 22, the ultrasonic observation part 104 of the present embodiment is constituted of an ultrasonic oscillator unit 108, a cylindrical sheathing member 110 for attaching and holding the ultrasonic oscillator unit 108, and the plurality of coaxial cables 58 of the shielded cable 72 wired to the ultrasonic oscillator unit 108.

As illustrated in FIG. 22, the ultrasonic oscillator unit 108 has an ultrasonic oscillator array 114 in which a plurality of ultrasonic oscillators 112 are arranged in a cylindrical shape; an electrode part 116 electrically connected to the ultrasonic oscillator array 114; a backing material layer 118 that supports the respective ultrasonic oscillators 112 of the ultrasonic oscillator array 114 from a surface (inner surfaces of the ultrasonic oscillators 112) side on a center side of the ultrasonic oscillator unit 108; an acoustic matching layer 120 laminated on the side (the outside of the ultrasonic oscillator array 114) of the ultrasonic oscillator array 114 opposite to of the backing material layer 118; and an acoustic lens 122 laminated on the side (the outside of the acoustic matching layer 120) of the acoustic matching layer 120 opposite to the ultrasonic oscillator array 114. As described above, the ultrasonic oscillator unit 108 has a laminated body 124 including the acoustic lens 122, the acoustic matching layer 120, the ultrasonic oscillator array 114, and the backing material layer 118.

Here, the electrode part 116 includes individual electrodes 116a of the plurality of ultrasonic oscillators 112 of the ultrasonic oscillator array 114, and a common electrode 116b common to the plurality of ultrasonic oscillators 112.

Additionally, the backing material layer 118 is supported by a cylindrical member 126 having a flange 126a disposed on a center side thereof.

In addition, although the ultrasonic oscillators 112, the ultrasonic oscillator array 114, the electrode part 116, the backing material layer 118, the acoustic matching layer 120, the acoustic lens 122, and the laminated body 124 of the present embodiment are geometrically different from the ultrasonic oscillator 48, the ultrasonic oscillator array 50, the electrode part 52, the backing material layer 54, the acoustic matching layer 64, the acoustic lens 66, and the laminated body 68 of the first embodiment illustrated in FIGS. 1 to 7, the configurations and functions thereof are the same. Thus, the description thereof is omitted.

Additionally, the ultrasonic oscillator unit 108 is electrically connected to the plurality of individual electrodes 116a of the electrode part 116, and a flexible wired board (FPC) 128 including a plurality of connecting parts 128a that wiring-connect the signal lines 58a of the plurality of coaxial cables 58; a ground bar 130 provided on the FPC 128 and electrically connected to the common electrode 116b of the electrode part 116; and a copper foil 132 disposed between the FPC 128 and the backing material layer 118 and pasted along a side end surface (an end surface on the endoscope observation part 106 side) of the cylindrical backing material layer 118 and an outer peripheral surface adjacent to the side end surface.

Here, the signal lines 58a of the plurality of coaxial cables 58 are electrically connected to the plurality of connecting parts 128a of the FPC 128, respectively, and the individual electrodes 116a of the plurality of ultrasonic oscillators 112 are electrically connected to the signal lines 58a of the plurality of coaxial cables 58, respectively.

Meanwhile, the shield members 58c of the plurality of coaxial cables 58 are electrically connected to the ground bar 130, and the common electrode 116b of the plurality of ultrasonic oscillators 112 is electrically connected to the shield members 58c of the plurality of coaxial cables 58.

In addition, one or more slits 126b passing through the inside and outside of the cylindrical member 126 open near an end part on a proximal end side of the laminated body 124 in the cylindrical member 126, and the plurality of coaxial cables 58, the signal lines 58a thereof, and the shield members 58c pass through the slits 126b, are pulled out to the outside from the inside of the cylindrical member 126, and are connected to the plurality of connecting parts 128a of the FPC 128 and the ground bar 130, respectively. In addition, the number of slits 126b may be one or multiple as long as the slits allow the plurality of coaxial cables 58, the signal lines 58a thereof, and the shield members 58c to pass therethrough.

Additionally, the copper foil 132 is thermally connected to the ground bar 130, and is thermally connected to the shield members 58c of the plurality of coaxial cables 58 via the ground bar 130.

Here, the copper foil 132 and the ground bar 130 shield the plurality of ultrasonic oscillators 112, and constitute a heat dissipation structure 134, serving as a feature the invention, which dissipates the heat generated in the plurality of ultrasonic oscillators 112 and the backing material layer 118 to the shield members 58c of the plurality of coaxial cables 58.

In this way, the heat generated in the plurality of ultrasonic oscillators 112 and the backing material layer 118 is dissipated to the outside of the subject through the insertion part (22) via the shield members 58c of the plurality of coaxial cables 58 by the heat dissipation structure 134 serving as the feature of the invention.

In the present embodiment, the copper foil 132 and the ground bar 130 may be integrated with each other in advance like the copper foil 62 and the ground bar 60 of the above-described first, second, and fourth embodiments, or may not be integrated with each other in advance and may be electrically and thermally connected to each other after the signal lines 58a of the plurality of coaxial cables 58 are electrically and thermally connected to each other in advance like the copper foil 62 and the ground bar 60 of the above-described third and fourth embodiments.

In addition, in the example illustrated in FIGS. 21 and 22, the copper foil 132 is folded and is connected to the ground bar 130 as in the above-described second embodiment. However, the invention is not limited to this.

Additionally, in the example illustrated in FIGS. 21 and 22, the FPC 128, the ground bar 130, and the copper foil 132 are provided on the endoscope observation part 38 side of the backing material layer 118. However, the invention is not limited to this, the FPC 128, and the ground bar 130, and the copper foil 132 may be provided on a distal end side of the distal end part 102, or any one of them may be provided on one side (for example, the endoscope observation part 38 side), and the remaining ones may be provided on the other side (for example, the distal end side of the distal end part 102).

Seventh Embodiment

FIG. 23 is a partially cross-sectional view schematically illustrating a distal end part of an insertion part of an ultrasonic endoscope of the present embodiment.

In addition, a distal end part 102a of an ultrasonic endoscope 100a of a seventh embodiment illustrated in FIG. 23 has the same configuration as the distal end part 102 of the ultrasonic endoscope 100 illustrated in FIG. 22 except for being different therefrom in that the collective ground 96 is provided instead of the ground bar 130 and the copper foil 132 disposed on a side end surface of the backing material layer 118 is thermally connected to the collective ground 96 via a second heat-conduction member 136. Thus, the same constituent elements will be designated by the same reference signs, and the description thereof will be omitted.

A heat dissipation structure 134a of an ultrasonic oscillator unit 108a of the distal end part 40a of the ultrasonic endoscope 100a illustrated in FIG. 23 has the collective ground 96 used in the fifth embodiment of the invention, the copper foil 132 that is the first heat-conduction member of the invention, and the second heat-conduction member 136 to which the copper foil 132 is thermally connected to the collective ground 96. Here, similarly to the sixth embodiment, the plurality of coaxial cables 58 and the signal lines 58a thereof pass through one or more slits 126b of the cylindrical member 126, are pulled out to the outside from the inside of the cylindrical member 126, and are connected to the plurality of connecting parts 128a of the FPC 128, respectively.

Additionally, the second heat-conduction member 136 connected to the copper foil 132 also passes through one or more slits 126b of the cylindrical member 126, is pulled from the outside of the cylindrical member 126 to the inside thereof, and is connected to the collective ground 96.

In addition, in the collective ground 96, the shield members 58c of the plurality of coaxial cables 58 including the front and the rear of the collective ground 96 serve as outer surfaces, and distal ends of the plurality of coaxial cables 58 connected to the plurality of connecting parts 128a of the FCP 128 are only the signal lines 58a. Between the collective ground 96 and the plurality of connecting parts 128a, the first insulating layer 58b serves as an outer surface, the signal lines 58a are covered with the first insulating layer 58b, and the plurality of signal lines 58a are insulated from each other.

Similarly to the second heat-conduction member 98 illustrated in FIG. 20, as long as the heat generated in the plurality of ultrasonic oscillators 112 and the backing material layer 118 and transferred to the copper foil 132 can be conducted to the collective ground 96, the second heat-conduction member 136 is not particularly limited. Any second heat-conduction member may be adopted as long as the second heat-conduction member has heat conductivity and is capable of being flexibly housed in a narrow space of the distal end part 102a of the ultrasonic endoscope 100a. As the second heat-conduction member 136, the same one as the second heat-conduction member 98 used in the fifth embodiment of the invention may be used.

In addition, in the distal end part 102 of the ultrasonic endoscope 100 illustrated in FIG. 22 and the distal end part 102a of the ultrasonic endoscope 100a illustrated in FIG. 23, it is preferable that a portion between the wiring portions, including the plurality of coaxial cables 58 scattered from the shielded cable 72 and the connecting parts of the signal lines 58a thereof, and the sheathing member 41 is filled with a filler material. As the filler material used in this case, any filler material can be used as long as the filler material is a non-conductive filler material, such as epoxy resin or silicon-based resin.

Although the ultrasonic endoscope and the method for manufacturing the ultrasonic endoscope related to the invention have been described above in detail, it is natural that the invention is not limited to the above examples, and various improvements and modifications may be made without departing from the scope of the invention.

EXPLANATION OF REFERENCES

10: ultrasonic inspection system
12, 12a, 100, 100a: ultrasonic endoscope
14: ultrasonic wave processor device
16: endoscope processor device
18: light source device
20: monitor
21a: water supply tank
21b: suction pump
22: insertion part
24: operating part
26: universal cord
28a: air/water supply button
28b: suction button
29: an angle knob
30: treatment tool insertion port (forceps port)
32a: ultrasonic wave connector
32b: endoscope connector
32c: light source connector
34a: air/water supply tube
34b: suction tube
36, 104: ultrasonic observation part
38, 106: endoscope observation part
40, 40a, 102, 102a: distal end part
41, 110: sheathing member
42: bending part
43: flexible part
44: treatment tool delivery port
45: treatment tool channel
46, 46a, 46b, 46c, 46d, 108,108a: ultrasonic oscillator unit
48, 112: ultrasonic oscillator 50, 114: ultrasonic oscillator array
52, 116: electrode part
52a, 116a: individual electrode
52b, 116b: common electrode
54, 118: backing material layer
56: cable wiring part
56a, 128a: connecting part
58: coaxial cable
58a: signal line
58b: first insulating layer
58c: shield member
58d: second insulating layer
60, 130: ground bar
62, 132: copper foil
64, 120: acoustic matching layer
66, 122: acoustic lens
68, 124: laminated body
70, 70a, 70b, 70c, 70d, 134, 134a: heat dissipation structure
72: shielded cable
72a: outer sheath
74: filler layer
76, 92: integrated member
78: observation window
80: objective lens
82: solid-state imaging element
84: illumination window
86: washing nozzle
88: wiring cable
90: wired board
94: wiring line
96: collective ground
98: second heat-conduction member
126: cylindrical member
126a: flange
126b: slit
128: flexible wired board (FPC)
136: second heat-conduction member
EL: longitudinal direction (elevation direction)
AZ: parallel direction (azimuth direction)

What is claimed is:

1. An ultrasonic endoscope comprising, at a distal end part thereof:
   an ultrasonic oscillator array in which a plurality of ultrasonic oscillators are arranged;
   a plurality of shielded cables each including a corresponding one of a plurality of signal lines, and a corresponding one of a plurality of metallic shield members disposed outside the corresponding one of the plurality of signal lines;
   a wiring part including a plurality of connecting parts that electrically connect the plurality of signal lines to the plurality of ultrasonic oscillators, respectively;
   a ground part comprising the plurality of shield members and having heat conductivity;
   a sheet-shaped first heat-conduction member disposed on a side surface of the ultrasonic oscillator array; and
   a second heat-conduction member that thermally connects the first heat-conduction member to the ground part,
   wherein the ultrasonic endoscope further comprises a backing material layer that is laminated on a back surface side of the ultrasonic oscillator array and supports the plurality of ultrasonic oscillators,
   wherein the first heat-conduction member is disposed on a side surface of a laminated body including the ultrasonic oscillator array and the backing material layer, and extends to a lower side of the backing material layer that is a side opposite to the ultrasonic oscillator array side,
   wherein the second heat-conduction member is connected to the first heat-conduction member at a lower end part of the first heat-conduction member that is the side opposite to the ultrasonic oscillator array side,
   wherein the plurality of shield members constitute the ground part, and are respectively connected to the second heat-conduction member integrated with the first heat-conduction member,
   wherein the first heat-conduction member integrated with the second heat-conduction member is pasted on the plurality of ultrasonic oscillators,
   wherein the first heat-conduction member is connected to the second heat-conduction member such that the lower end part of the first heat-conduction member on the side opposite to the ultrasonic oscillator array is directed to an upper side that is the ultrasonic oscillator array side, and
   wherein an upper end part side of the first heat-conduction member is folded toward the side surface of the laminated body, and is pasted on the plurality of ultrasonic oscillators.

2. The ultrasonic endoscope according to claim 1,
   wherein each of the plurality of shielded cables is at least one of a plurality of coaxial cables or a non-coaxial cable,
   wherein each of the plurality of coaxial cables respectively includes a signal line at a center side thereof and a shield member on an outer peripheral side of the signal line, and
   wherein the non-coaxial cable is a cable in which the corresponding one of the plurality of signal lines and a drain line as the corresponding one of the plurality of shield members are disposed in a mixed manner, or a cable in which the corresponding one of the plurality of signal lines is disposed on a center side of the cable, and a conducting wire is disposed as the corresponding one of the plurality of shield members around the corresponding one of the plurality of signal lines.

3. The ultrasonic endoscope according to claim 1,
   wherein the first heat-conduction member and the second heat-conduction member are conductive members,
   wherein the plurality of connecting parts of the wiring part electrically connect the plurality of signal lines to the plurality of ultrasonic oscillators, respectively, using first solder,
   wherein the plurality of shield members are connected to the second heat-conduction member using the first solder, respectively, and
   wherein the first heat-conduction member is connected to the second heat-conduction member, using at least one of second solder having a lower melting point than the first solder, silver paste, or a conductive adhesive.

4. The ultrasonic endoscope according to claim 1,
   wherein the second heat-conduction member is a bar connected to the plurality of shielded cables.

5. The ultrasonic endoscope according to claim 1,
   wherein the second heat-conduction member is a wired board including a bar connected to the plurality of shielded cables, and
   wherein the first heat-conduction member is connected to a position on the wired board electrically joined to the bar.

6. The ultrasonic endoscope according to claim 1,
wherein the first heat-conduction member is metallic foil having electrical conductivity and heat conductivity.

7. The ultrasonic endoscope according to claim 6,
wherein the metallic foil is copper foil, aluminum foil, or gold foil.

8. The ultrasonic endoscope according to claim 1,
wherein the plurality of shielded cables are wrapped to form one cable.

9. An ultrasonic endoscope comprising, at a distal end part thereof:
an ultrasonic oscillator array in which a plurality of ultrasonic oscillators are arranged;
a plurality of shielded cables each including a corresponding one of a plurality of signal lines, and a corresponding one of a plurality of metallic shield members disposed outside the corresponding one of the plurality of signal lines;
a wiring part including a plurality of connecting parts that electrically connect the plurality of signal lines to the plurality of ultrasonic oscillators, respectively;
a ground part comprising the plurality of shield members and having heat conductivity;
a sheet-shaped first heat-conduction member disposed on a side surface of the ultrasonic oscillator array; and
a second heat-conduction member that thermally connects the first heat-conduction member to the ground part,
wherein the first heat-conduction member and the second heat-conduction member are conductive members,
wherein the plurality of connecting parts of the wiring part electrically connect the plurality of signal lines to the plurality of ultrasonic oscillators, respectively, using first solder,
wherein the plurality of shield members are connected to the second heat-conduction member using the first solder, respectively,
wherein the first heat-conduction member is connected to the second heat-conduction member, using at least one of second solder having a lower melting point than the first solder, silver paste, or a conductive adhesive,
wherein the first heat-conduction member is connected to the second heat-conduction member such that a lower end part of the first heat-conduction member on a side opposite to the ultrasonic oscillator array is directed to an upper side that is an ultrasonic oscillator array side, and
wherein an upper end part side of the first heat-conduction member is folded toward a side surface of a laminated body, and is pasted on the plurality of ultrasonic oscillators.

10. The ultrasonic endoscope according to claim 9,
wherein each of the plurality of shielded cables is at least one of a plurality of coaxial cables or a non-coaxial cable,
wherein each of the plurality of coaxial cables respectively includes a signal line at a center side thereof and a shield member on an outer peripheral side of the signal line, and
wherein the non-coaxial cable is a cable in which the corresponding one of the plurality of signal lines and a drain line as the corresponding one of the plurality of shield members are disposed in a mixed manner, or a cable in which the corresponding one of the plurality of signal lines is disposed on a center side of the cable, and a conducting wire is disposed as the corresponding one of the plurality of shield members around the corresponding one of the plurality of signal lines.

11. The ultrasonic endoscope according to claim 9,
wherein the second heat-conduction member is a bar connected to the plurality of shielded cables.

12. The ultrasonic endoscope according to claim 9,
wherein the second heat-conduction member is a wired board including a bar connected to the plurality of shielded cables, and
wherein the first heat-conduction member is connected to a position on the wired board electrically joined to the bar.

13. The ultrasonic endoscope according to claim 9,
wherein the first heat-conduction member is metallic foil having electrical conductivity and heat conductivity.

14. The ultrasonic endoscope according to claim 13,
wherein the metallic foil is copper foil, aluminum foil, or gold foil.

15. The ultrasonic endoscope according to claim 9,
wherein the plurality of shielded cables are wrapped to form one cable.

16. A method of manufacturing an ultrasonic endoscope, the method comprising:
when manufacturing the ultrasonic endoscope according to claim 1,
integrating the first heat-conduction member and the second heat-conduction member in advance at the lower end part of the first heat-conduction member that is the side opposite to the ultrasonic oscillator array side;
connecting the plurality of shield members of the plurality of shielded cables to the second heat-conduction member integrated with the first heat-conduction member in advance, respectively;
then, connecting the plurality of signal lines of the plurality of shielded cables, including the plurality of shield members connected to the second heat-conduction member integrated with the first heat-conduction member in advance, to the plurality of connecting parts of the wiring part, respectively, using solder, and electrically connecting the plurality of signal lines to the plurality of ultrasonic oscillators; and
pasting the first heat-conduction member integrated with the second heat-conduction member to the plurality of ultrasonic oscillators, and disposing the first heat-conduction member on the side surface of the laminated body including the ultrasonic oscillator array and the backing material layer that is laminated on the back surface side of the ultrasonic oscillator array and supports the plurality of ultrasonic oscillators.

17. The method for manufacturing an ultrasonic endoscope according to claim 16,
wherein in the step of connecting the plurality of shield members to the second heat-conduction member, respectively, the second heat-conduction member integrated with the first heat-conduction member is situated to the side opposite to the ultrasonic oscillator array side, and the plurality of shield members are connected to the second heat-conduction member, respectively, and
wherein in the step of disposing the first heat-conduction member on the side surface of the laminated body, the first heat-conduction member is pasted on the plurality of ultrasonic oscillators and is disposed on the side surface of the laminated body in a state where the first heat-conduction member is folded, and a side of first heat-conduction member opposite to a side thereof to which the second heat-conduction member is connected is the ultrasonic oscillator array side.

18. The method for manufacturing an ultrasonic endoscope according to claim 16,
wherein the second heat-conduction member is a bar, and
wherein in the step of integrating the first heat-conduction member and the second heat-conduction member with each other in advance, the bar and the first heat-conduction member are electrically connected to each other by integrating a wired board including the bar, and the first heat-conduction member with each other in advance.

19. A method of manufacturing an ultrasonic endoscope, the method comprising:
when manufacturing the ultrasonic endoscope according to claim 1,
pasting the first heat-conduction member to the plurality of ultrasonic oscillators, and disposing the first heat-conduction member on the side surface of the laminated body including the ultrasonic oscillator array and the backing material layer that is laminated on the back surface side of the ultrasonic oscillator array and supports the plurality of ultrasonic oscillators;
connecting the plurality of shield members of the plurality of shielded cables to the second heat-conduction member, using solder, respectively;
connecting the plurality of signal lines of the plurality of shielded cables to the plurality of connecting parts of the wiring part, respectively, using the solder, and electrically connecting the plurality of signal lines to the plurality of ultrasonic oscillators; and
connecting the first heat-conduction member to the second heat-conduction member, using at least one of solder having a lower melting point than the solder, silver paste, or a conductive adhesive.

20. A method of manufacturing an ultrasonic endoscope, the method comprising:
when manufacturing the ultrasonic endoscope according to claim 9,
pasting the first heat-conduction member to the plurality of ultrasonic oscillators, and disposing the first heat-conduction member on the side surface of the laminated body including the ultrasonic oscillator array and a backing material layer that is laminated on a back surface side of the ultrasonic oscillator array and supports the plurality of ultrasonic oscillators;
connecting the plurality of shield members of the plurality of shielded cables to the second heat-conduction member, using solder, respectively;
connecting the plurality of signal lines of the plurality of shielded cables to the plurality of connecting parts of the wiring part, respectively, using the solder, and electrically connecting the plurality of signal lines to the plurality of ultrasonic oscillators; and
connecting the first heat-conduction member to the second heat-conduction member, using at least one of solder having a lower melting point than the solder, silver paste, or a conductive adhesive.

* * * * *